(12) United States Patent
Eddy et al.

(10) Patent No.: US 11,529,088 B2
(45) Date of Patent: Dec. 20, 2022

(54) MODULAR CARDIAC RHYTHM MANAGEMENT USING Q TO LV ACTIVATION MEASURES

(71) Applicant: CARDIAC PACEMAKERS, INC., St. Paul, MN (US)

(72) Inventors: Steven Lee Eddy, Chesterfield, VA (US); Brendan Early Koop, Ham Lake, MN (US); Yinghong Yu, Shoreview, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 208 days.

(21) Appl. No.: 17/080,182

(22) Filed: Oct. 26, 2020

(65) Prior Publication Data
US 2021/0106271 A1    Apr. 15, 2021

Related U.S. Application Data

(63) Continuation of application No. 15/943,612, filed on Apr. 2, 2018, now Pat. No. 10,849,522.
(Continued)

(51) Int. Cl.
*A61B 5/352* (2021.01)
*A61B 5/00* (2006.01)
(Continued)

(52) U.S. Cl.
CPC .............. *A61B 5/352* (2021.01); *A61B 5/283* (2021.01); *A61B 5/287* (2021.01); *A61B 5/349* (2021.01);
(Continued)

(58) Field of Classification Search
CPC ................ A61N 1/36842; A61N 1/056; A61N 1/37258; A61N 1/37264; A61N 1/37288; A61N 1/3756
See application file for complete search history.

(56) References Cited

U.S. PATENT DOCUMENTS 6,165,166 A    12/2000   Samuelson et al.
8,103,359 B2    1/2012   Reddy
(Continued)

FOREIGN PATENT DOCUMENTS

EP    2204127 A1    7/2010
EP    2473228 A1    7/2012
(Continued)

OTHER PUBLICATIONS

Koop, Brendan Early, Implantable Medical Device Delivery System With Integrated Sensor, U.S. Appl. No. 62/413,748, filed Oct. 27, 2016.
(Continued)

*Primary Examiner* — Brian T Gedeon
(74) *Attorney, Agent, or Firm* — Seager, Tufte & Wickhem LLP

(57) ABSTRACT

Methods and systems for use of the Q-wave to R-wave interval to guide placement of a leadless cardiac pacemaker are disclosed. An implant delivery device is equipped with sensing electrodes to sense R-wave onset in a ventricle of a patient's heart to allow placement at a location of last or latest onset of the R-wave. Guidance tools are provided to assist in determination of the Q-wave to R-wave interval during implantation. For a chronic system, a cooperative approach is disclosed in which an implantable medical device and a leadless cardiac pacemaker exchange data to determine Q-wave to R-wave intervals and enhance cardiac resynchronization therapy delivery by the leadless cardiac pacemaker.

20 Claims, 21 Drawing Sheets

Related U.S. Application Data

(60) Provisional application No. 62/480,591, filed on Apr. 3, 2017.

(51) Int. Cl.

| | | |
|---|---|---|
| *A61N 1/05* | (2006.01) | |
| *A61N 1/372* | (2006.01) | |
| *A61N 1/375* | (2006.01) | |
| *A61N 1/368* | (2006.01) | |
| *A61B 5/283* | (2021.01) | |
| *A61B 5/287* | (2021.01) | |
| *A61B 5/349* | (2021.01) | |

(52) U.S. Cl.
CPC .............. *A61B 5/686* (2013.01); *A61N 1/056* (2013.01); *A61N 1/36842* (2017.08); *A61N 1/3756* (2013.01); *A61N 1/37258* (2013.01); *A61N 1/37264* (2013.01); *A61N 1/37288* (2013.01); *A61B 5/0006* (2013.01); *A61B 5/4836* (2013.01); *A61B 2560/066* (2013.01)

(56) References Cited

U.S. PATENT DOCUMENTS

| | | |
|---|---|---|
| 8,565,878 B2 | 10/2013 | Allavatam et al. |
| 10,500,395 B2 | 12/2019 | Soltis et al. |
| 2006/0085041 A1 | 4/2006 | Hastings et al. |
| 2011/0160801 A1 | 6/2011 | Markowitz et al. |
| 2015/0025612 A1 | 1/2015 | Haasl et al. |
| 2015/0051610 A1 | 2/2015 | Schmidt et al. |
| 2015/0224320 A1 | 8/2015 | Stahmann |
| 2015/0297902 A1* | 10/2015 | Stahmann ............ A61N 1/3621 607/4 |
| 2015/0360036 A1 | 12/2015 | Kane et al. |
| 2016/0030747 A1 | 2/2016 | Thakur et al. |
| 2016/0059025 A1 | 3/2016 | Stahmann et al. |
| 2016/0089539 A1 | 3/2016 | Gilkerson et al. |
| 2017/0021159 A1 | 1/2017 | Reddy et al. |
| 2017/0291022 A1* | 10/2017 | Shuros ..................... A61N 1/00 |
| 2018/0036527 A1 | 2/2018 | Reddy et al. |

FOREIGN PATENT DOCUMENTS

| | | |
|---|---|---|
| WO | 2011028949 A1 | 3/2011 |
| WO | 2012091747 A1 | 7/2012 |
| WO | 2014087337 A1 | 6/2014 |

OTHER PUBLICATIONS

Hahn, Stephen J., Integrated Multi-Device Cardiac Resynchronization Therapy Using P-Wave to Pace Timing, U.S. Appl. No. 62/378,880, filed Aug. 24, 2016.

Hahn, Stephen J., Cardiac Resynchronization Using Fusion Promotion for Timing Management, U.S. Appl. No. 62/378,866, filed Aug. 24, 2016.

Hahn, Stephen J., Cardiac Therapy System Using Subcutaneously Sensed P-Waves for Resynchronization Pacing Management, U.S. Appl. No. 62/355,121, filed Jun. 27, 2016.

Stahmann, Jeffrey E., LCP Based Predictive Timing for Cardiac Resynchronization, U.S. Appl. No. 62/424,582, filed Nov. 21, 2016.

An, Qi, Method and System for Determining an Atrial Contraction Timing Fiducial in a Leadless Cardiac Pacemker System, U.S. Appl. No. 62/359,055, filed Jul. 6, 2016.

\* cited by examiner

MODULAR CARDIAC RHYTHM MANAGEMENT USING Q TO LV ACTIVATION MEASURES

CROSS REFERENCE TO RELATED APPLICATIONS

The present application is a continuation of U.S. patent application Ser. No. 15/943,612, filed Apr. 2, 2018 and titled MODULAR CARDIAC RHYTHM MANAGEMENT USING Q TO LV ACTIVATION MEASURES, now U.S. Pat. No. 10,849,522, which claims the benefit of and priority to U.S. Provisional Patent Application No. 62/480,591, filed Apr. 3, 2017 and titled MODULAR CARDIAC RHYTHM MANAGEMENT USING Q TO LV ACTIVATION MEASURES, the disclosures of which are incorporated herein by reference.

BACKGROUND

Cardiac resynchronization therapy (CRT) modifies the electrical activation and contractions of the heart's chambers to enhance pumping efficiency. Benefits may include increased exercise capacity and reduced hospitalization and mortality. More particularly, CRT devices operate by affecting the timing of contraction of one or more cardiac chambers relative to one or more other cardiac chambers. For example, contractions of one or more of the ventricle(s) may be timed relative to contraction of the atria, or contractions of the left and right ventricles may be timed relative to one another.

A "fusion" beat occurs when multiple activation signals affect the same cardiac tissue at the same time. For example, electrical fusion between pacing of one ventricle with spontaneous activation of another ventricle (for example, paced left ventricular (LV) activation and intrinsic right ventricular (RV) activation) produces a fusion beat. The generation of fusion beats is a goal of CRT in many circumstances.

Prior systems generally include intracardiac electrodes coupled via transvenous leads to an implanted pulse generator. The leads of such systems are widely known as introducing various morbidities and are prone to eventual conductor and/or insulator failure. Such issues likely reduce usage of CRT within the indicated population of heart failure patients.

Such prior lead systems typically include ventricular and atrial components to facilitate sensing of atrial and ventricular events to enhance CRT timing. For example, in some patients, CRT may be achieved by pacing the left ventricle at a specific time relative to detection of an atrial event. The sensed atrial signal may conduct to the RV via natural conduction to generate an RV contraction, with paced LV contraction occurring at a desirable time relative to the RV contraction to yield a fusion beat. The interval from the atrial sensed event to the LV pace may be adjusted to enhance cardiac response in prior systems.

Newer generation pacemakers include the leadless cardiac pacemaker (LCP), which can be implanted entirely within the heart and does not require a transvenous (or any) lead. Such devices are commercially available on a limited basis, but are currently indicated for and capable of use in only bradycardia pacing. With further enhancements, the LCP also presents an opportunity to provide an alternative to traditional CRT using transvenous leads. However, the LCP, if placed for example in or on the LV, may not have visibility to cardiac electrical activity in other chambers. New and alternative systems, devices and methods directed at providing CRT using the LCP are desired.

OVERVIEW

The present inventors have recognized, among other things, that a problem to be solved is the need to optimize LV pacing therapy when provided using an LCP. In some examples, intraoperative monitoring of the Q-wave and LV activation may be performed during implantation of an LCP to identify an implant location demonstrating desirable electrical activation characteristics. In some examples, postoperative and/or ambulatory monitoring from an extracardiac location, such as in the thorax and outside the heart, or even outside of the ribcage, may be performed to monitor for P-waves and/or Q-waves to support manipulation of LV pace timing in order to optimize atrioventricular (AV) delay.

A first non-limiting example takes the form of a method of implanting a leadless cardiac pacemaker (LCP), the method of implant using an LCP delivery system comprising a handle assembly, an shaft extending distally from the handle assembly and including a distal region, and an LCP containment housing coupled to the distal region of the shaft and extending distally therefrom, the LCP containment housing adapted for holding the LCP during implantation thereof to a patient's heart, wherein the distal region and/or LCP containment housing comprise a plurality of electrodes adapted to sense cardiac signals during implantation of the LCP; the method comprising: inserting the LCP containment housing into a blood vessel of the patient and advancing the LCP containment housing and at least a portion of the shaft into the blood vessel to bring the LCP containment housing into adjacency with a portion of the myocardium; using the electrodes of the LCP delivery system to capture electrical signals for one or more cardiac cycles while the containment housing is adjacent to the portion of the myocardium to identify a ventricular activation time for the myocardium adjacent the containment housing; capturing a surface electrocardiogram for the patient and identifying a Q-wave for at least one of the one or more cardiac cycles; manipulating the handle to adjust the position of the containment housing relative to the myocardium to identify a location on the myocardium of latest ventricular activation relative to a Q-wave identified on the surface electrocardiogram; and implanting the LCP at the location of the myocardium resulting in the latest ventricular activation relative to the Q-wave.

A second, non-limiting example takes the form of a method of implanting a leadless cardiac pacemaker (LCP), the method of implant using an LCP delivery system comprising a handle assembly, an shaft extending distally from the handle assembly and including a distal region, and an LCP containment housing coupled to the distal region of the shaft and extending distally therefrom, the LCP containment housing adapted for holding the LCP during implantation thereof to a patient's heart, wherein the distal region and/or LCP containment housing comprise a plurality of electrodes adapted to sense cardiac signals during implantation of the LCP; the method comprising: inserting the LCP containment housing into a blood vessel of the patient and advancing the LCP containment housing and at least a portion of the shaft into the blood vessel to bring the LCP containment housing proximity with a portion of the myocardium; using the electrodes of the LCP delivery system to capture one or more cardiac cycles while the containment housing is adjacent to the portion of the myocardium to sense a ventricular activation time for the myocardium adjacent the containment housing; capturing a surface electrocardiogram for the patient and identifying a Q-wave for at least one of the one or more cardiac cycles; determining a Q-wave to ventricular activation interval and comparing it to an interval threshold and, if the threshold is not exceeded determining that the portion of the myocardium is not a suitable location for implanting the LCP, and manipulating the handle to adjust the position of the containment housing relative to the myocardium to identify a location on the myocardium of later ventricular activation relative to a Q-wave identified on the surface electrocardiogram; and implanting the LCP at a location of the myocardium at which the interval threshold is exceeded.

Additionally or alternatively to the first or second non-limiting examples, the one or more electrodes may be located at a distal tip of the LCP containment housing.

Additionally or alternatively to the first or second non-limiting examples, the electrodes may be electrically coupled to a port at the handle, and the method comprises using an external ECG analysis device configured to capture the surface electrocardiogram and perform the step of comparing the segment of the cardiac signal to the surface electrocardiogram to provide information to a person manipulating the handle.

A third non-limiting example takes the form of a medical device implantation system for implanting a leadless cardiac pacemaker (LCP) to the heart of a patient, the system comprising: an LCP delivery system adapted for implanting an LCP having a proximal end with a handle for manipulating a position of the LCP in a patient and a distal end having a housing for holding the LCP during an implantation procedure, the distal end of the implantation tool comprising one or more electrodes for capturing cardiac signals during implantation of the LCP; an implant guidance device comprising a first input for obtaining a cardiac signal from surface electrodes on a patient and a second input for obtaining a cardiac signal from the LCP delivery system, a user interface for providing an output to a user, and operational circuitry configured to calculate a QR interval by comparing an EGM obtained from the electrodes of the LCP delivery system to an ECG to calculate a QR interval, wherein the timing of the Q wave of the QR interval is obtained from the ECG, and the timing of the R wave of the QR interval is obtained from the EGM, wherein the operational circuitry is further configured to provide audible or visual feedback to an implanting person regarding suitability of a location for implantation of the LCP using the QR interval.

Additionally or alternatively to the third non-limiting example, the operational circuitry may be configured to: indicate via the user interface that a user should manipulate the position of the LCP containment housing relative to the patient's heart; repeatedly calculate QR intervals as the user manipulates the position of the LCP containment housing relative to the patient's heart; and identify a peak of the QR intervals and generate an output signal using the user interface indicating the peak, wherein the peak indicates a longer QR interval than at least one other calculated QR interval.

Additionally or alternatively to the third non-limiting example, the implant guidance device may be configured for use during implantation of an LCP to the left ventricle, further wherein the QR intervals are calculated for an interval from the Q-wave as determined using the ECG to the R-wave as sensed in the left ventricle.

Additionally or alternatively to the third non-limiting example, the implant guidance device may be configured to identify the peak of the QR intervals by identifying termination of the R-wave in the ECG and determining that the R-wave from the EGM is within a threshold interval from termination of the R-wave from the ECG.

Additionally or alternatively to the third non-limiting example, the operational circuitry may be configured to compare the QR interval to a threshold for LCP implant acceptability, and, if the threshold is exceeded, to provide an audible or visual indication of acceptability of a position for the LCP.

Additionally or alternatively to the third non-limiting example, the operational circuitry may be configured to compare the QR interval to a threshold for LCP implant acceptability, and, if the threshold is not exceeded, to provide an audible or visual indication that a position for the LCP is not acceptable.

Additionally or alternatively to the third non-limiting example, the operational circuitry may be configured to set the threshold for LCP implant acceptability as a fraction of a known QRS width for a patient.

A fourth non-limiting example takes the form of an implantable medical device (IMD) configured for use with a leadless cardiac pacemaker (LCP) implanted in the left ventricle or coronary sinus of a patient, the IMD adapted to communicate with the LCP while implanted using wireless or conducted communication, the IMD comprising: a plurality of electrodes for sensing cardiac electrical activity; operational circuitry for analyzing the sensed cardiac electrical activity and determining whether and what to communicate to the LCP; wherein the operational circuitry is configured to perform the following: identify one or more cardiac cycles; calculate a measure of Q-wave to left ventricle (LV) R-wave peak timing for one or more cardiac cycles; and communicate to the LCP to cause the LCP to adjust a therapy regimen using at least the measure of Q-wave to LV R-wave peak timing.

Additionally or alternatively to the fourth non-limiting example, the IMD may further comprise a posture sensor for sensing a patient's posture, wherein the operational circuitry is configured to calculate an adjustment to the LCP therapy regimen by determining an optimal Q-wave to LV pace timing using the measured Q-wave to LV R-wave peak timing and the patient posture.

Additionally or alternatively to the fourth non-limiting example, wherein the operational circuitry may be configured to identify a plurality of at least 2 cardiac cycles and calculate a composite cardiac cycle signal, and to calculate the measure of Q-wave to LV R-wave peak timing using the composite cardiac cycle signal.

Additionally or alternatively to the fourth non-limiting example, the operational circuitry may be configured to include a plurality of modes for calculating an adjustment to the LCP therapy including: a first mode for use with an LCP implanted in or in a tributary to the coronary sinus; and a second mode for use with an LCP implanted in the LV.

Additionally or alternatively to the fourth non-limiting example, the operational circuitry may be configured to identify a Q-wave using the sensed cardiac signal, and to obtain timing information from the LCP regarding an LV R-wave occurring in the same cardiac cycle as the identified Q-wave, and thereby calculate the Q-wave to LV R-wave peak timing.

Additionally or alternatively to the fourth non-limiting example, the operational circuitry may be configured to identify a plurality of at least 2 cardiac cycles and calculate a composite cardiac cycle signal, to identify a Q-wave in the composite cardiac cycle signal for the at least 2 cardiac cycles, to obtain LV R-wave timing for the at least 2 cardiac cycles from the LCP, and thereby calculate the Q-wave to LV R-wave peak timing.

A fifth non-limiting example takes the form of a system comprising an IMD as in the fourth non-limiting example, and any of the above additions or alternatives thereto, and a leadless cardiac pacemaker (LCP) comprising electrodes for therapy output and/or cardiac signal reception, an LCP communication module for communicating with at least the IMD, a pulse generator module for generating pacing output signals, and a processing module for managing a therapy regimen provided via the pulse generator module, the processing module adapted to effecting changes to the therapy regimen in response to signals from the IMD captured via the LCP communication module.

Additionally or alternatively to the fifth non-limiting example, the processing module may be adapted to interrupt the therapy output of the pulse generator to pause for at least one intrinsic cardiac cycle to allow the IMD to analyze the intrinsic Q-wave to LV R-wave peak timing.

Additionally or alternatively to the fifth non-limiting example, the LCP may comprise a sensing module adapted to sense an intrinsic R-wave during the pause, and the processing module is adapted to cause the LCP communication module to generate a communication of timing of the sensed intrinsic R-wave to the IMD for use in calculating the Q-wave to LV R-wave peak timing.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Cardiac pacemakers provide electrical stimulation to heart tissue to cause the heart to contract and thus pump blood through the vascular system. Transvenous pacemakers include an electrical lead that extends from a pulse generator implanted subcutaneously or sub-muscularly through one or more blood vessels to an electrode positioned in or on the heart. Epicardial pacemakers include an electrical lead that extends from a pulse generator implanted subcutaneously or submuscularly to an electrode or electrode pair attached to the outside wall of the cardiac chamber.

As an alternative, self-contained or leadless cardiac pacemakers have been proposed. Leadless cardiac pacemakers are small capsules that may, for example, be fixed to an intracardiac implant site in a cardiac chamber. In some cases, the small capsule may include bipolar pacing/sensing electrodes, a power source (e.g. a battery), and associated electrical circuitry for controlling the pacing/sensing electrodes, and thus may provide electrical stimulation to heart tissue and/or sense a physiological condition.

Figure 1:
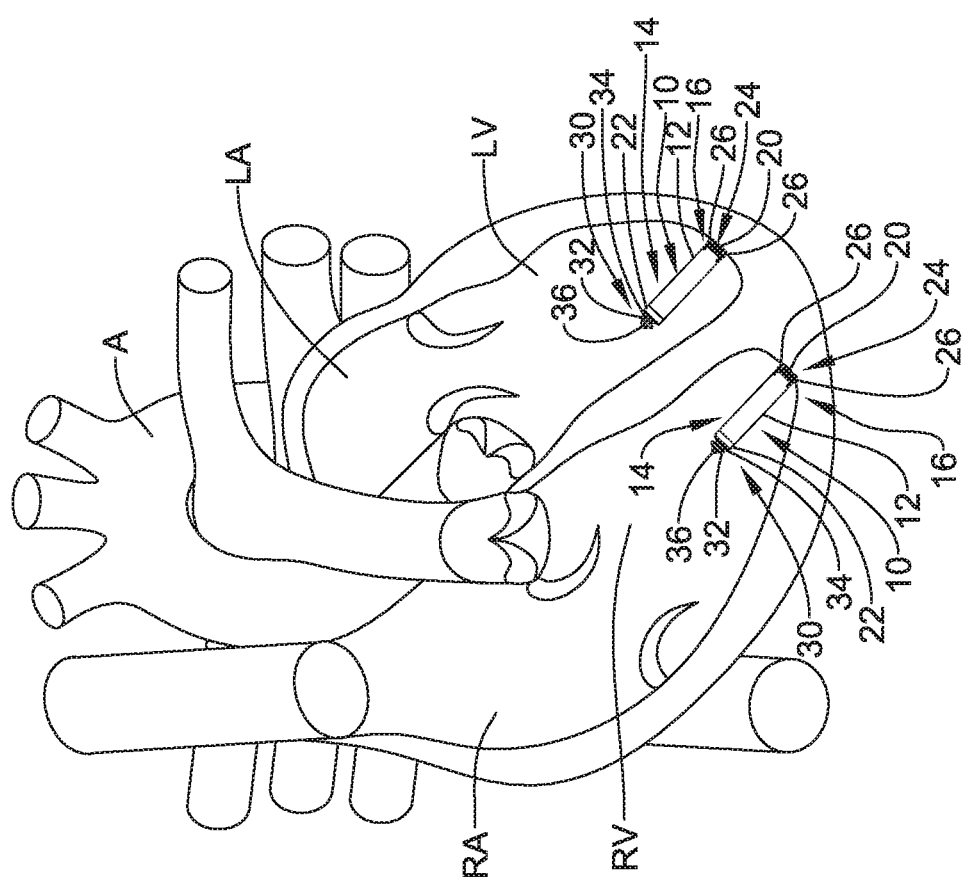
FIG. 1 shows an illustrative implantable leadless cardiac pacemaker implanted in the heart of a patient.

FIG. 1 illustrates example implantable leadless cardiac pacing devices 10 (e.g., a leadless pacemaker or LCP 10) implanted in a patient's heart. An illustrative LCP 10 is shown within the right ventricle (RV) while another LCP 10 is shown within the left ventricle (LV) as the LCP 10 may be configured for implantation in either ventricle, or in another chamber such as a right atrium (RA) or a left atrium (LA). In another example, implantation may be to the coronary sinus (CS) or a tributary branch off the CS on or over the LV, rather than into the LV. Implantation may also be performed in the epicardial coronary vein (ECV). Depending on therapeutic needs, a patient may have a single LCP 10 or may have two or more LCPs 10 implanted in or adjacent appropriate chambers.

Figure 2:
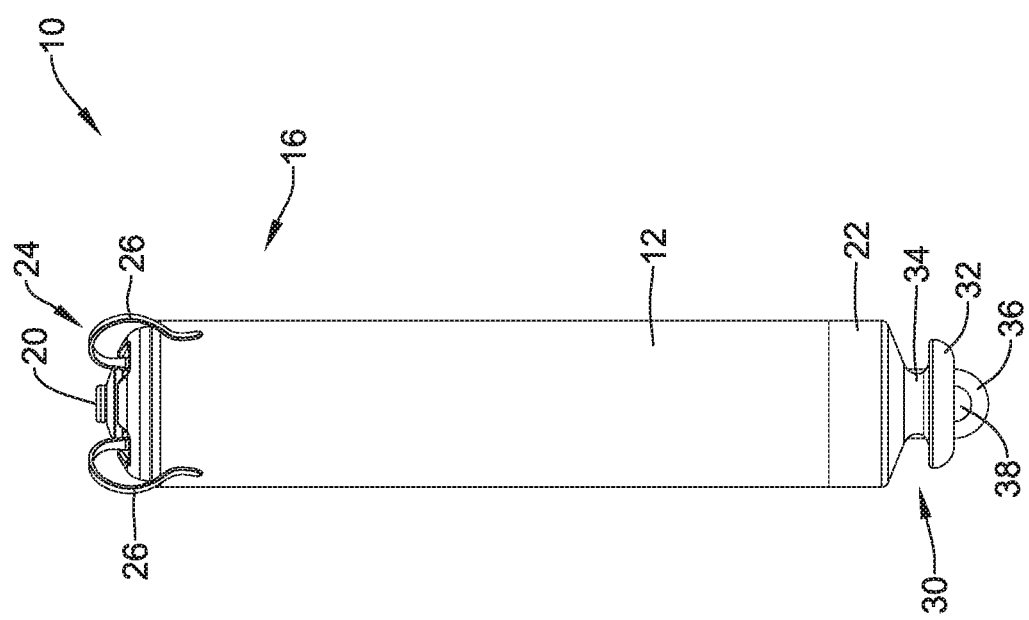
FIG. 2 shows an illustrative implantable leadless cardiac pacemaker.

A side view of the illustrative LCP 10 is shown in FIG. 2. The LCP 10 may include a shell or housing 12 having a proximal end 14 and a distal end 16. In some instances, the LCP 10 may include a first electrode 20 positioned adjacent to the distal end 16 of the housing 12 and a second electrode 22 positioned adjacent to the proximal end 14 of the housing 12. In some cases, the housing 12 may include a conductive material and may be insulated along at least a portion of its length. A section along the proximal end 14 may be free of insulation so as to define the second electrode 22. The electrodes 20, 22 may be used to provide electrical therapy and/or sensing capabilities. The first electrode 20 may be configured to be positioned against the cardiac tissue of the heart or may otherwise contact the cardiac tissue of the heart while the second electrode 22 may be spaced away from the first electrode 20, and thus spaced away from the cardiac tissue.

Figure 15:
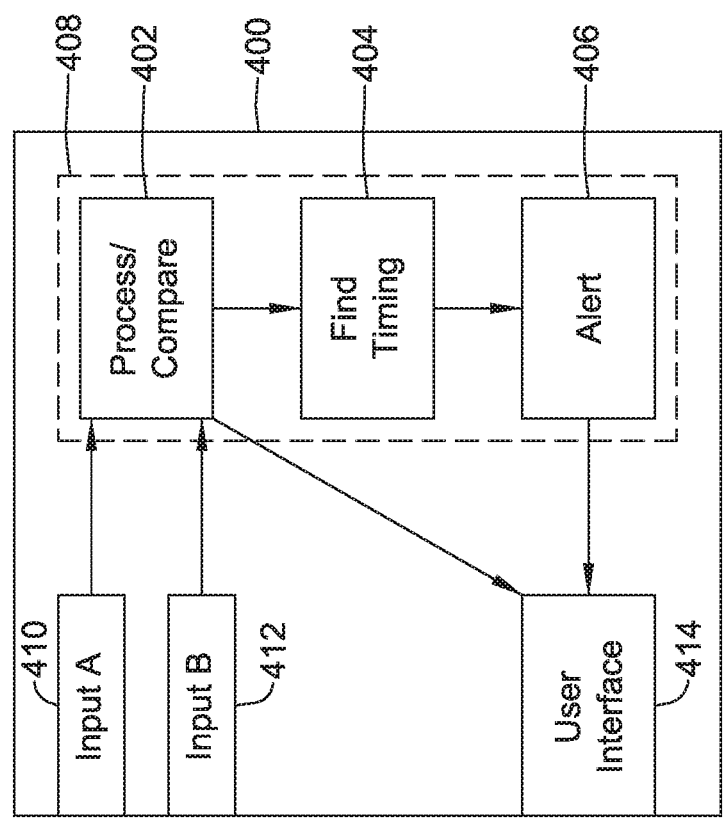
FIG. 15 shows an illustrative implant placement guidance device.

The LCP 10 may include a pulse generator (e.g., electrical circuitry) and a power source (e.g., a battery) within the housing 12 to provide electrical signals to the electrodes 20, 22 and thus control the pacing/sensing electrodes 20, 22. In some cases, current or voltage may be delivered to the electrodes 20, 22 may provide electrical stimulation to heart tissue and/or sense a physiological condition or, in some examples, to communicate to another implantable medical device emplaced in the same patient, or to an external device such as a programmer. FIG. 15, below, provides some details as to the operational circuitry that may be included.

The LCP 10 may include a fixation mechanism 24 at or near the distal end 16 of the housing 12 configured to attach the LCP 10 to a cardiac tissue wall, or otherwise anchor the LCP 10 to the anatomy of the patient. As shown in FIG. 1, in some instances, the fixation mechanism 24 may include one or more hooks or tines 26 anchored into the cardiac tissue to attach the LCP 10 to a tissue wall. In other cases, the fixation mechanism 24 may include one or more passive tines, configured to entangle with trabeculae within the chamber of the heart and/or a helical fixation anchor configured to be screwed into a tissue wall to anchor the LCP 10 to the heart.

The LCP 10 may include a docking member 30 near the proximal end 14 of the housing 12 configured to facilitate delivery and/or retrieval of the LCP 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the LCP 10 which is greater than a radial dimension of the neck portion 34 from the longitudinal axis of the LCP 10.

The docking member 30 may further include a tether retention structure 36 extending from the head portion 32. The tether retention structure 36 may define an opening 38 configured to receive a tether or other anchoring mechanism therethrough. While the retention structure 36 is shown as having a generally U-shaped configuration, the retention structure 36 may take any shape which provides an enclosed perimeter surrounding the opening 38 such that a tether may be securably and releasably passed (e.g. looped) through the opening 38. The retention structure 36 may extend though the head portion 32, along the neck portion 34, and to or into the proximal end 14 of the housing 12. The docking member 30 may be configured to facilitate delivery of the LCP 10 to the intracardiac site and/or retrieval of the LCP 10 from the intracardiac site. Other docking members 30 are contemplated.

In some cases, the LCP 10 may include one or more sensors or other devices that facilitate tracking the LCP 10 during and/or after delivery. In some cases, the sensor may be considered to represent one or more magnetic tracking sensors that may facilitate magnetic tracking of the LCP 10 using a system such as described in U.S. Provisional Patent Application 62/413,748, titled IMPLANTABLE MEDICAL DEVICE DELIVERY SYSTEM WITH INTEGRATED SENSOR the disclosure of which is incorporated herein by reference.

In some cases, the LCP 10 may be delivered to the heart using a delivery device which may be advanced through a femoral vein, into the inferior vena cava, into the right atrium, through the tricuspid valve, and into the RV. The target region for the delivery of the LCP 10 may instead be a portion of the LV. In another example, the target placement for the LCP may be in the CS (or a tributary thereof), using for example, the methods and devices in U.S. Pat. No. 8,103,359, a tributary to the CS, or the ECV. Accordingly, it will be appreciated that the delivery device may need to be navigated through relatively tortuous anatomy to deliver the LCP 10 to a suitable location. The target region may also include other regions of the heart (e.g., right atrium, left atrium, or left ventricle), other blood vessels, or other suitable targets. It may be desirable to provide the delivery system with certain features that may allow for easier or better control for navigation or delivery purposes.

As noted, in some examples implantation of the LCP 10 may be to the coronary sinus. To secure a device in place in the coronary sinus or other larger cardiac vessels, an expandable member such as a stent may be provided in attachment to the LCP. The LCP may also or instead include a short lead having on it a securing/placement device such as an expandable stent, or a pigtail lead or an expandable loop such as shown in U.S. Pat. No. 8,103,359, the disclosure of which is incorporated herein by reference. In another example, the LCP can be placed in the rather large coronary sinus with a short lead advanced into a nearby and smaller tributary vessel where the anchoring mechanism may be secured. As shown in the U.S. Pat. No. 8,103,359 patent, a device containment housing may be used to constrain an expandable member and hold the LCP during advancement through the patient's vasculature until a desired position is reached. As shown below, such a device containment housing may be provided with further features for position optimization using cardiac signal sensing during advancement and placement.

Figure 3:
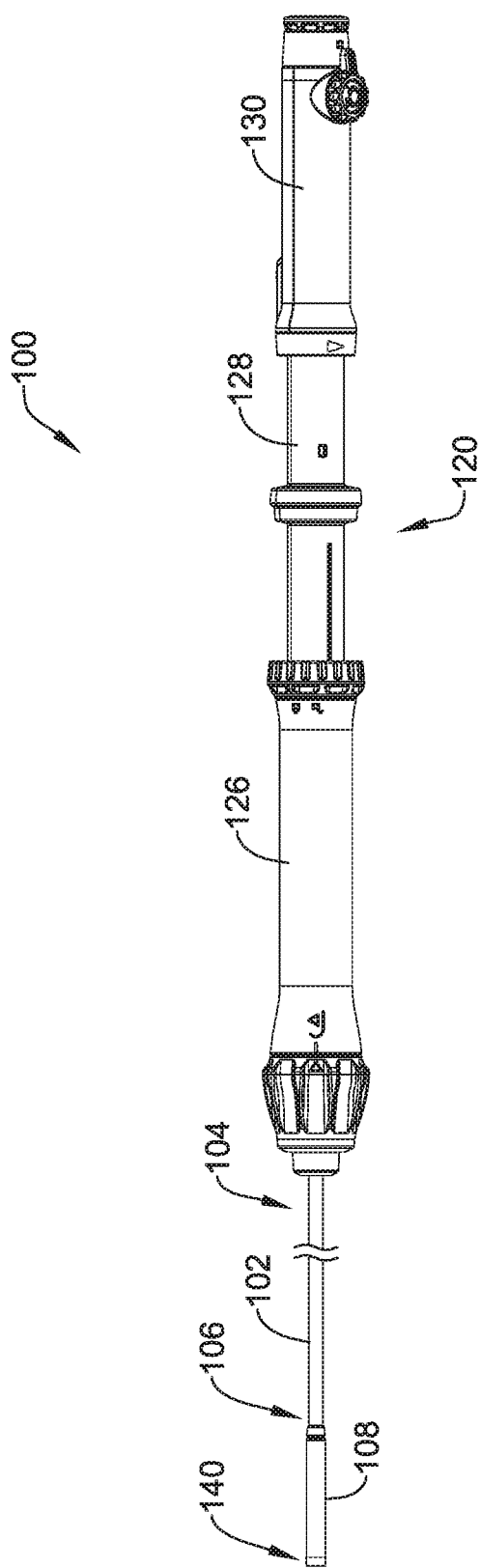
FIG. 3 shows an example delivery device for a leadless cardiac pacemaker.

FIG. 3 is a plan view of an illustrative delivery device 100, such as a catheter, that may be used to deliver the LCP 10. It will be appreciated that the delivery device 100 is merely illustrative, as the LCP 10 may be delivered with other delivery devices that may or may not include some of the features described with respect to the delivery device 100. As illustrated, the delivery device 100 may include an outer tubular member 102 having a proximal section 104 and a distal section 106. Extensive discussion of the delivery device 100 may be found, for example, in U.S. Provisional Application No. 62/413,748, titled IMPLANTABLE MEDICAL DEVICE DELIVERY SYSTEM WITH INTEGRATED SENSOR, the disclosure of which is incorporated herein by reference The delivery device 100 may also include a handle assembly 120 positioned adjacent to the proximal section 104 of the outer tubular member 102. The handle assembly 120 may include a first or distal hub portion 126 attached to, such as fixedly attached to, the proximal end section 104 of the outer tubular member 102. In some examples, the device containment housing 108 may be secured to the outer tubular member 102 and thereby to the distal hub 126. In other examples, an intermediate tubular member couples the device containment housing 108 to a second or intermediate hub portion 128. A third or proximal hub portion 130 attached to, such as fixedly attached to, a proximal end section of an inner tubular member which has a distal end that, in this example, extends to the containment housing and may be used to push a device distally out from within the containment housing. The first hub portion 126, second hub portion 128, and third hub portion 130 may be positioned in a generally telescoping arrangement and longitudinally slidable and/or rotatable relative to each other.

The device containment housing 108 may be configured to receive the LCP 10 therein. For example, the device containment housing 108 may define a cavity for slidably receiving the LCP 10, and may include a distal opening for slidable insertion and/or extraction of the LCP 10 into and/or out of the cavity. The device containment housing 108 may include a distal tip portion 140 that may be, for example, configured to be atraumatic to anatomy, such as a bumper tip. For example, as the catheter is navigated through the anatomy, the distal tip 140 may come into contact with vascular anatomy. Additionally, when the catheter is used to deliver the implantable medical device 10, the tip 140 of the delivery device 100 will likely come into contact with tissue adjacent the target site (e.g. cardiac tissue of the heart). Thus a soft distal tip may reduce the risk of harm to such anatomy. In some particular embodiments, the durometer of the material used in the distal tip 140 may be in the range of about 5 D to about 70 D, or for example, in the range of about 25 D to about 65 D. Additionally, the distal tip 140 may include a shape or structure that may make it less traumatic to tissue. For example, the distal tip 140 may have a distal surface, such as a tissue contacting surface, that is that is rounded or includes a curvature configured to be more atraumatic to tissue.

In some instances, all or a portion of the device containment housing 108 may include an inner surface that may be configured to resist getting caught on the fixation mechanism 24, such as the one or more hooks or tines 26 on the implantable medical device 10. For example, the device containment housing 108 may include an inner layer or coating of harder or more lubricious material that resists force applied by the fixation mechanism 24 onto the inner surface of the device containment housing 108. For example, the device containment housing 108 may include a multi-layered structure, and an inner layer may be made of a material that is harder and/or more lubricious than an outer layer. For example a trilayer structure may be used with a soft outer layer of material and a lubricious inner layer, with a tie layer therebetween as shown in U.S. Pat. No. 6,165,166.

A tether 112 (shown in FIG. 4, below) or other retaining feature may be used to releasably secure the LCP 10 to the delivery device 100. In some instances, the tether 112 may be a single or unitary length of material that may extend from a proximal end of the device 100 through the opening 38 of the LCP 10 and return to the proximal hub or third 130. In some instances, the ends of the tether 112 may be secured within a locking feature in the third hub portion 130. Additional tether details, including designs and mechanisms for securing and releasing a tether, may be found in U.S. Provisional Application No. 62/413,748, titled IMPLANTABLE MEDICAL DEVICE DELIVERY SYSTEM WITH INTEGRATED SENSOR, the disclosure of which is incorporated herein by reference.

In order to more specifically place or steer the delivery device 100 to a position adjacent to the intended target, the delivery device 100 may be configured to be deflectable or articulable or steerable. Designs and mechanisms for steering, curvature, manipulation, shape member, etc., are further discussed in U.S. Provisional Application No. 62/413,748, titled IMPLANTABLE MEDICAL DEVICE DELIVERY SYSTEM WITH INTEGRATED SENSOR, the disclosure of which is incorporated herein by reference. The handle assembly 120 may include one or more ports for delivering fluids, such as, but not limited to, a contrast and/or flushing fluid to the cavity of the device containment housing 108.

Figure 4:
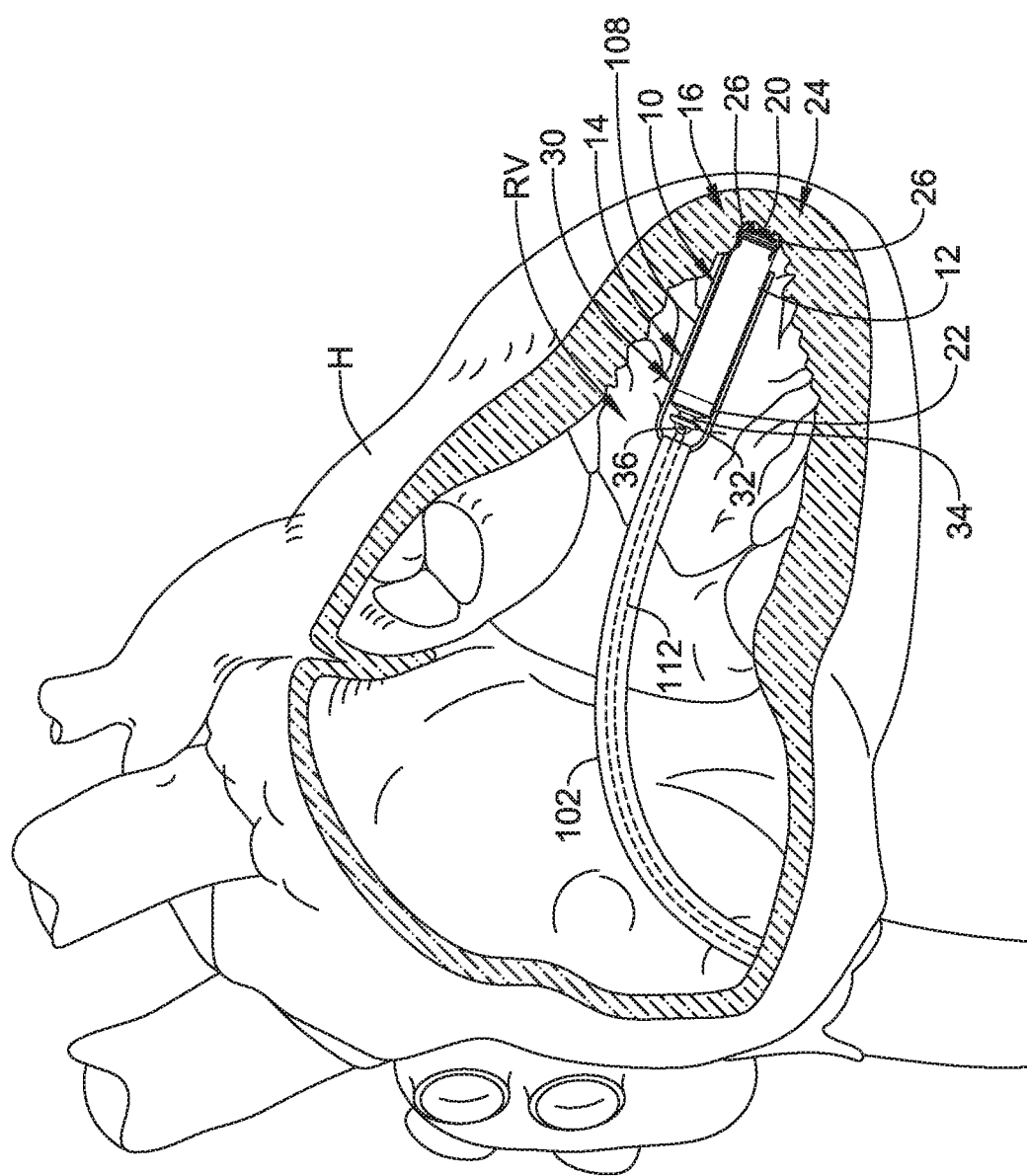
FIG. 4 shows use of the delivery device to implant/deploy a leadless cardiac pacemaker.

FIG. 4 illustrates part of a method for deploying an LCP 10 using a delivery device as shown in FIG. 3. For simplicity, these Figures show the LCP 10 being delivered to the right ventricle RV. The delivery device 100 may be introduced into the vasculature through the femoral vein through a previously introduced guide catheter, for example. It will be appreciated that the LCP 10 may be delivered and deployed in the left ventricle LV via an intra-aortic approach or through the left atrium LA, for example. The delivery device 100 may be introduced through any desired location and with or without the use of a guide catheter as desired.

The delivery device 100 may be advanced through the vasculature to the desired treatment location, which, in the case of a leadless cardiac pacing device, may be a chamber of the heart. The clinician may manipulate a steering mechanism, for example, to deflect the distal section 106 of the outer tubular member 102 in a desired manner to facilitate advancement of the delivery device 100. During advancement of the delivery device 100, the LCP 10 may be contained and secured in the device containment housing using, for example, the tether 112 to hold the LCP 10 in place.

Figure 5:
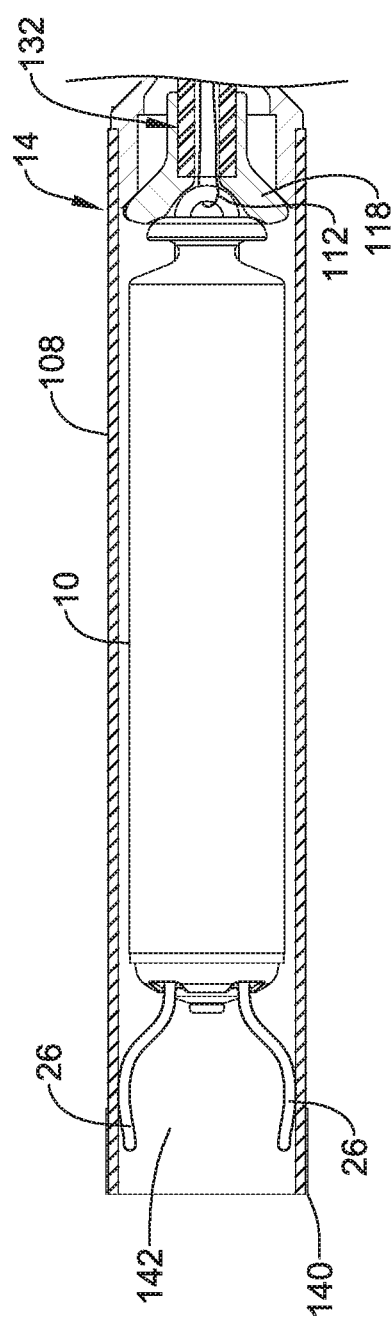
FIG. 5 shows a leadless cardiac pacemaker in a pre-implantation or delivery state within a device containment housing of a delivery device.

Upon achieving a desired position, the clinician may use the proximal handle as shown in FIG. 3 to push the LCP 10 out of the device containment housing. FIG. 5 is illustrative of the pre-deployment state and also how of such pushing occurs. The LCP 10 is shown in a pre-deployment state inside the device containment housing 108. The device containment housing 108 includes the bumper tip 140 as described above. An inner surface 142 of the device containment housing 108 may be slippery or of a hard polymer to make sliding of the LCP 10 relatively easy.

The tether 112 is shown attaching to the proximal end of the LCP 10 to hold it in place. An inner tubular member 132, which can be manipulated from the proximal hub 130 of the handle is shown with a pusher 118 at the distal end thereof, with the tether 114 extending in a hollow inner lumen of the inner tubular member 132. In this manner, the inner tubular member 132 can be used to push the LCP 10 out of the device containment housing 108 while the tether remains secure. The fixation mechanism in this example is shown as a plurality of tines 26, which are biased to curl outward as shown in FIG. 2, above, when unrestrained by the device containment housing 108.

Once the distal tip portion 140 of the device containment housing 108 has been positioned adjacent to the cardiac tissue where the LCP 10 is desired, deployment of the LCP 10 can begin. The first stage of deploying the LCP 10 may enable activation of the fixation mechanism. To initiate the first stage of deployment, the clinician may stabilize the first hub portion 126 relative to the patient. The clinician may then slide the third hub portion 130 distally. As the inner tubular member 132 advances distally, the distal portion 118 may "push" against the proximal end 14 of the implantable medical device 10.

As the LCP 10 is pushed distally, the hooks 26 engage the heart tissue as shown in FIG. 4. The LCP 10 may be distally advanced out of the device containment housing 108 to deploy the hooks or tines 26 to engage in the heart tissue while the proximal portion of the LCP 10 remains within the device containment housing 108. In some instances, the LCP 10 may be advanced distally in the range of 1 to 5 millimeters, although this is merely illustrative.

The proximal structure of the delivery device can be used to allow advancement of the LCP 10 a relatively short distance first to engage the hooks or tines 26 to the cardiac tissue. By limiting the forward movement initially, risks of cardiac perforation, for example, may be reduced. After the cardiac tissue is engaged by the hooks or tines 26, the device containment housing 108 is withdrawn relative to the pusher 118, LCP 10, and nearby cardiac tissue to release the LCP 10 from the device containment housing, leaving only the tether 112 attached to the LCP 10. Details of locking mechanisms and the like for such a process may be found, for example, in U.S. Provisional Application No. 62/413,748, titled IMPLANTABLE MEDICAL DEVICE DELIVERY SYSTEM WITH INTEGRATED SENSOR, the disclosure of which is incorporated herein by reference.

Attachment to the cardiac tissue may be tested by gently tugging on the LCP 10 using the tether 112, optionally while observing the process using a visualization system such as x-ray, fluoroscopy and/or a sophisticated system such as the RHYTHMIA® system available from Boston Scientific. Functional testing of the LCP 10 may be performed to ensure adequate signal sensing and/or to ensure that the LCP 10 can effectively deliver therapy having an intended outcome at the implant position. If such testing fails, the tether 112 can be used to guide and draw the LCP 10 back into the device containment housing 108 for repositioning, as desired.

FIGS. 6-12 provide illustrative but non-limiting examples of how the delivery device 100 in general, and the device containment housing 108 in particular, may be modified to help in testing possible implantation sites.

Figure 6:
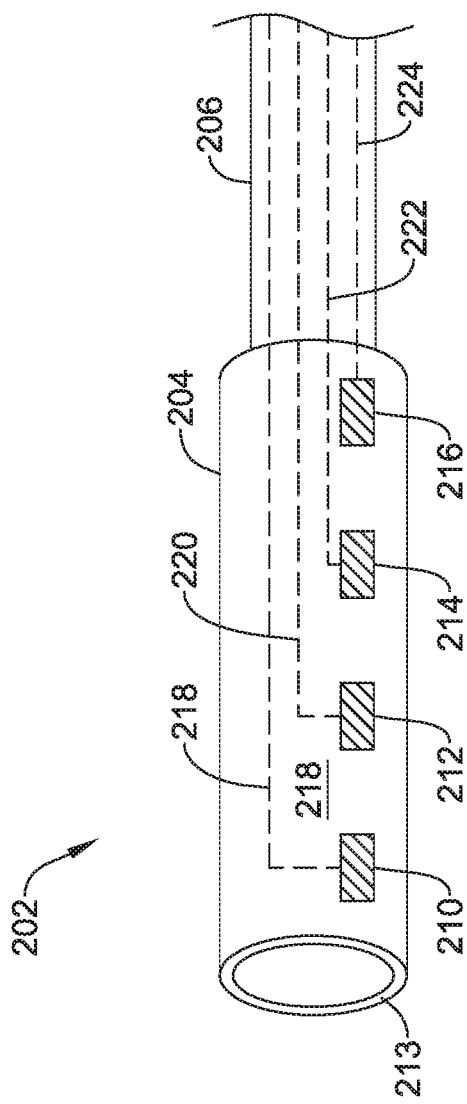
FIGS. 6-12 show illustrative distal portions of a delivery device showing features of several designs for device containment housings.

FIG. 6 is a schematic diagram of a portion of an illustrative delivery device 202, which may be considered as being an example of the delivery device 100. In some cases, as illustrated, the delivery device 202 includes a device containment housing 204 extending distally from a shaft 206. In some cases, the device containment housing 204 may be considered as being an example of the device containment housing 108. In this example, the device containment housing 204 includes several electrodes 210, 212, 214, 216 that may be used in electrically testing a possible implantation site. The electrodes 210, 212, 214, 216 may, for example, be disposed on an outer surface 208 of the device containment housing 204 in axially and/or radially spaced configuration(s). The electrodes 210, 212, 214, 216 may be rectangular, as shown, or oval or circular or any other shape. The electrodes 210, 212, 214, 216 may be all the same shape and size, or may encompass a plurality of shapes or sizes on a single device. The electrodes may themselves extend in axial and/or radial directions about the surface of the device containment housing 204.

A plurality of electrical connectors 218, 220, 222, 224 are shown with distal terminations at the electrodes 210, 212, 214, 216. The electrical connectors 218, 220, 222, 224 may be small electrically conductive wires that extend through the delivery device to or near to its proximal end, with a port/plug provided in association with, for example, any of the hubs shown above for coupling to an external device to monitor the electrical signals of tissue near the device containment housing during implantation, to support methods discussed further below.

In some examples, the electrodes 210, 212, 214, 216 may be used to capture intrinsic cardiac signals, or to capture pace-induced cardiac signals, if desired. In some examples, the electrodes 210, 212, 214, 216 may be used to deliver a non-stimulating electrical output in bipolar or monopolar configurations to generate impedance data, either by monitoring a voltage induced at electrodes that are not used to deliver the electrical output, or by monitoring characteristics of the electrical output itself.

In some cases, conductivity values obtained via electrodes on the device containment housing 204 may, for example, be used to determine heart wall contact. For example, blood has a lower conductivity compared to tissue such as cardiac tissue. A relatively lower conductivity value may indicate a lack of tissue contact while a relatively higher conductivity value may indicate tissue contact, for example. In some cases, tissue composition may impact conductivity. For example, infarcted tissue has more collagen than healthy myocardium, and thus a conductivity value may be useful in determining whether a possible implantation site includes healthy myocardium or unhealthy myocardium, which can be important in achieving lower pacing threshold values.

Figure 7:
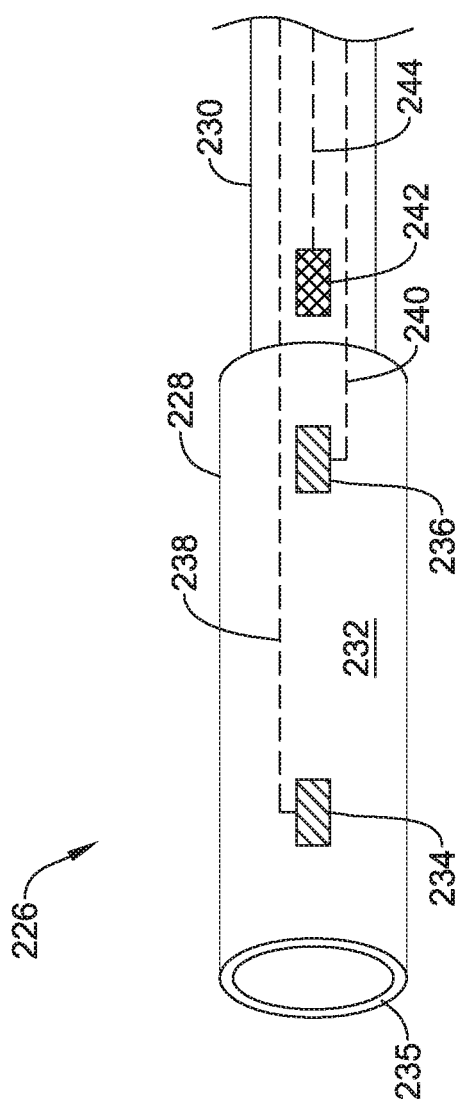
Figure 8:
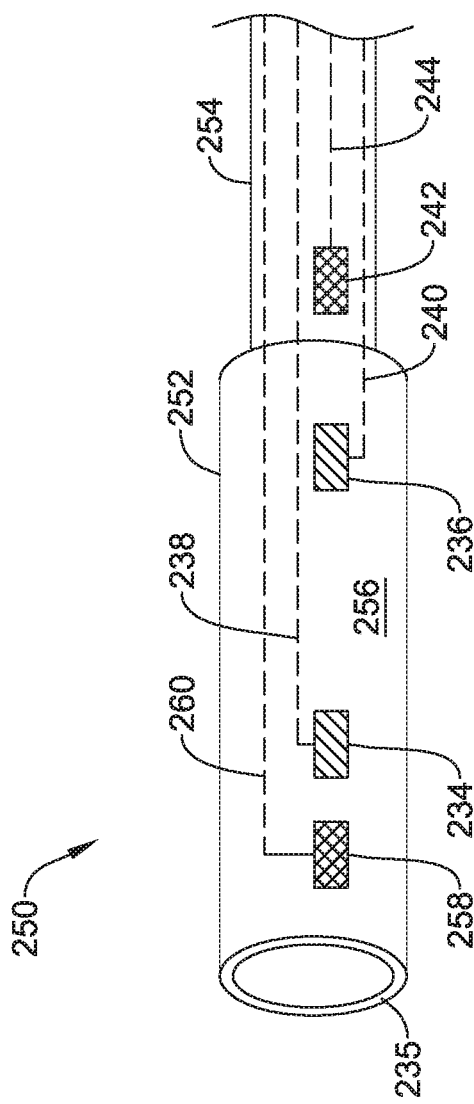

FIG. 7 shows another example showing an illustrative delivery device 226, which may be considered as being an example of the delivery device 100. In some cases, as illustrated, the delivery device 226 includes a device containment housing 228 extending distally from a shaft 230. In some cases, the device containment housing 228 may be considered as being an example of the device containment housing 108. In this instance, only two electrodes 236, 234 are shown on the device containment housing 238. Associated electrical conductors are shown at 238, 240, extending toward the proximal end of the device. One or the other of the electrodes 234, 236 may extend over the distal end 235 of the device containment housing 228 so as to directly engage tissue when the distal end 235 of the device containment housing 228 is pushed up against a heart wall.

An additional sensor 242 is shown with its own electrical connector 244. The additional sensor may be on the more proximal shaft of the delivery device 226, as shown, or may be on the device containment housing 228 instead. In some cases, for example, the sensor 242 may be a pressure sensor such as a piezoelectric pressure sensor and may be configured to provide a signal representative of blood pressure within a cardiac chamber that results from a stimulation pulse applied by the electrodes 234, 236. In some cases, the sensor 242 may instead represent an accelerometer or an acoustic sensor that can output a signal representative of cardiac performance in response to an applied stimulation pulse (e.g. heart sounds, heart wall acceleration, etc.). In some cases, the sensor 242 may represent a gyroscope that can output a signal representative of cardiac performance (e.g. twist) in response to an applied stimulation pulse. In some cases, the sensor 242 may include electronic components to amplify, filter or otherwise condition a raw sensor signal. In some cases, the sensor 242 may be a bidirectional transducer (e.g. a bidirectional acoustic transducer to facilitate ultrasound measurements). In some examples, the sensor 242 may be a strain gauge to measure strain on the shaft of the delivery device, to indicate to the clinician how much pressure is being applied by the device containment housing against a cardiac or vascular tissue wall and provide an alert or warning if a strain threshold is exceeded.

In some cases, a delivery device may include multiple sensors and multiple electrodes. As shown for example in FIG. 8, a delivery device 250 may include a device containment housing 252 extending from shaft 254, and may be considered as being an example of the delivery device 100. In some cases, the device containment housing 252 may be considered as being an example of the device containment housing 108. In some cases, as seen, the device containment housing 252 has an outer surface 256 and includes the first electrode 234 and the second electrode 236. In some cases, the first electrical connector 238 extends proximally from the first electrode 234 and the second electrical connector 240 extends proximally from the second electrode 212.

In some cases, a sensor 242 may represent a first pressure sensor and a sensor 258 may represent a second pressure sensor. The sensor 242 is shown operably coupled to the electrical connector 244 while the sensor 258 is shown operably coupled to an electrical connector 260 that extends proximally from the sensor 258 and thus may be operably coupled with a programmer, tester or other device. In some cases, for example, the sensor 242 and the sensor 258 may each be piezoelectric pressure sensors, or other types of pressure sensors, and may each be configured to provide a signal representative of blood pressure within a cardiac chamber that results from a stimulation pulse applied as a potential difference between the first electrode 234 and the second electrode 236, for example. In some cases, it will be appreciated that depending on the exact position of the delivery device 250 with respect to the patient's heart, the sensor 242 and the sensor 258 may see different pressure waveforms that may be useful in determining the appropriateness of a particular possible implantation site. For example, in some cases, the sensor 242 may see an atrial pressure waveform while the sensor 258 may see a ventricular pressure waveform. These may be useful in determining an A-V delay, for example.

Figure 9:
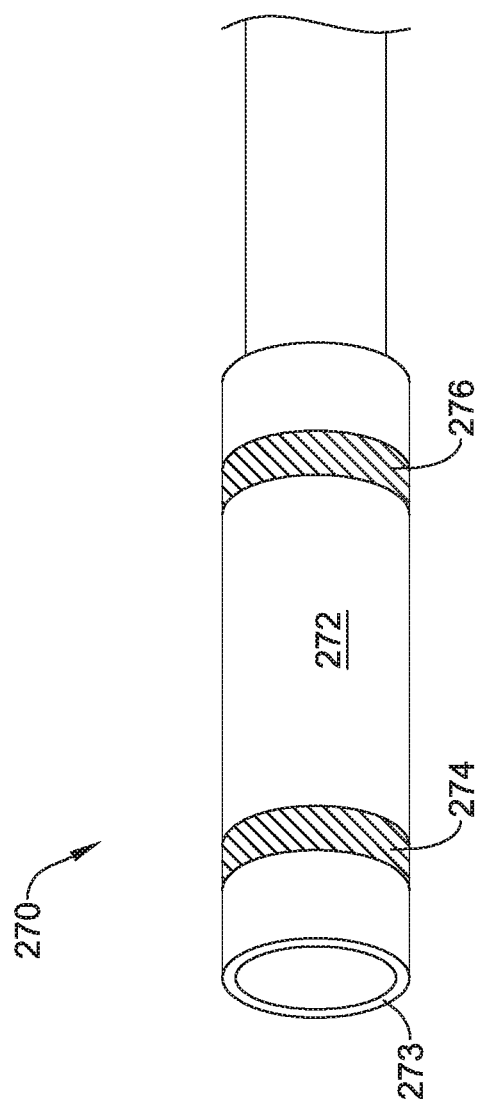

FIG. 9 shows another example. Here a device delivery tool is shown at 270 with a distally located device containment housing at 272. Two ring electrodes 274, 276 are disposed on the device containment housing 272 (conductors for the ring electrodes are not shown). Greater area and coverage of these ring electrodes may be useful to obtain a less localized signal than the smaller electrode. Ring electrode 274 may, optionally, be at or extend at least partly over the distal tip 273 of the device containment housing 272.

Figure 10:
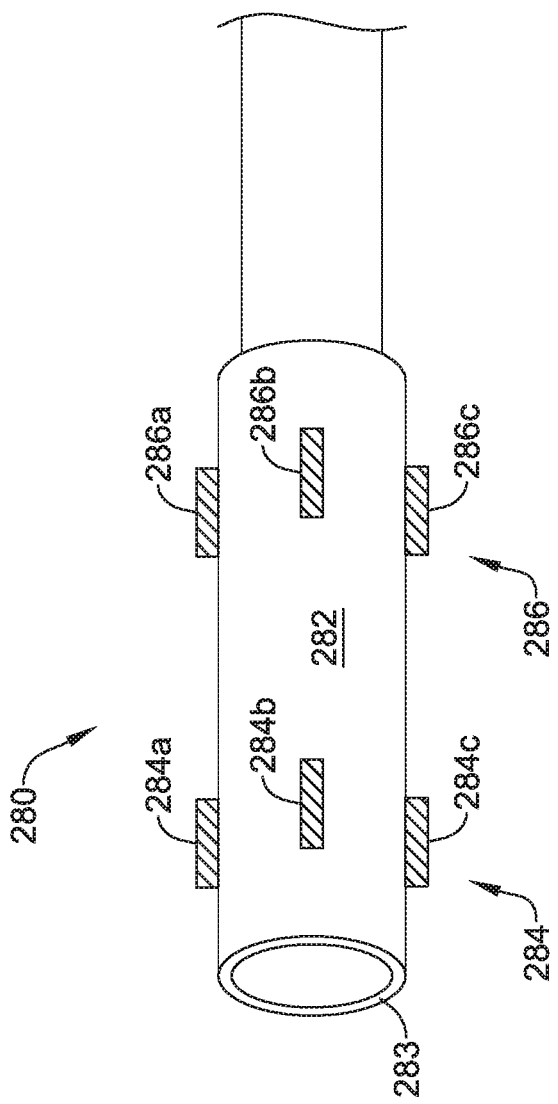

FIG. 10 shows a device containment housing 280 that has an outer surface 282. A first electrode array 284 and a second electrode array 286 can be seen to be disposed on the outer surface 282. In some cases, as illustrated, the first electrode array 284 includes an electrode 284a, an electrode 284b and an electrode 284c. The first electrode array 284 may include additional electrodes not visible in this view. Similarly, the second electrode array 286 may include an electrode 286a, an electrode 286b and an electrode 286c. The second electrode array 286 may include additional electrodes not visible in this view. In some cases, each of the electrodes 284a, 284b, 284c may be electrically coupled together. In some instances, each of the electrodes 284a, 284b, 284c may be individually addressable. While not explicitly shown, in some cases each of the electrodes 284a, 284b, 284c may extend over the distal end 283 of the device containment housing 280 so as to directly engage tissue when the distal end 283 of the device containment housing 280 is pushed up against a heart wall. In some cases, each of the electrodes 286a, 286b, 286c may be electrically coupled together. In some instances, each of the electrodes 286a, 286b, 286c may be individually addressable.

It will be appreciated that by having electrodes that extend at least partially, if not entirely, around the outer surface 282, there may be fewer issues with making tissue/blood contact regardless of rotational orientation of the device containment housing 280 relative to the heart H. While two electrode arrays 284, 286 are shown, it will be appreciated that the device containment housing 280 may include three, four or more electrode arrays. In some cases, the device containment housing 280 may also include one or more sensors that are configured to provide a signal representative of cardiac performance.

Figure 11:
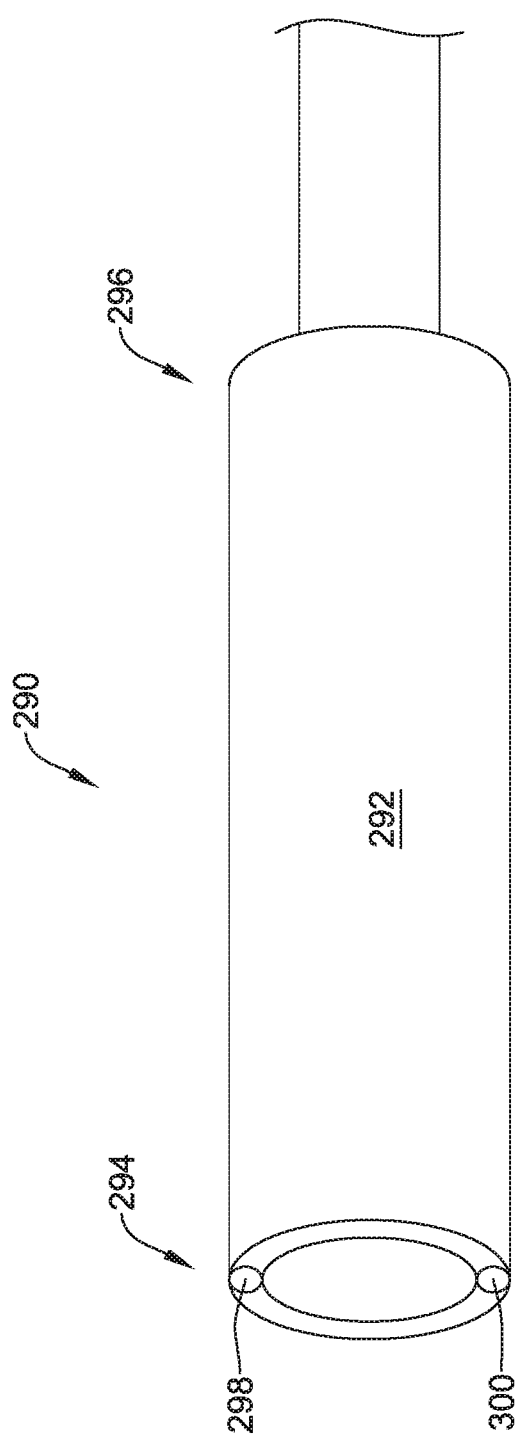

FIG. 11 is a schematic illustration of a device containment housing 290 including features that may be combined with any of the device containment housings 204, 228 and 252, above. The illustrative device containment housing 290 includes an outer surface 292 that extends from a distal end 294 to a proximal end 296. The distal end 294 may include a plurality of electrodes 298, 300 that can be used for tissue contact verification as well as to detect cardiac signals at the distal tip 294. Electrical conductors (not shown) may extend to the proximal end of the delivery device. Additional electrodes may be disposed on the sidewalls of the device containment housing 290 as well.

Figure 12:
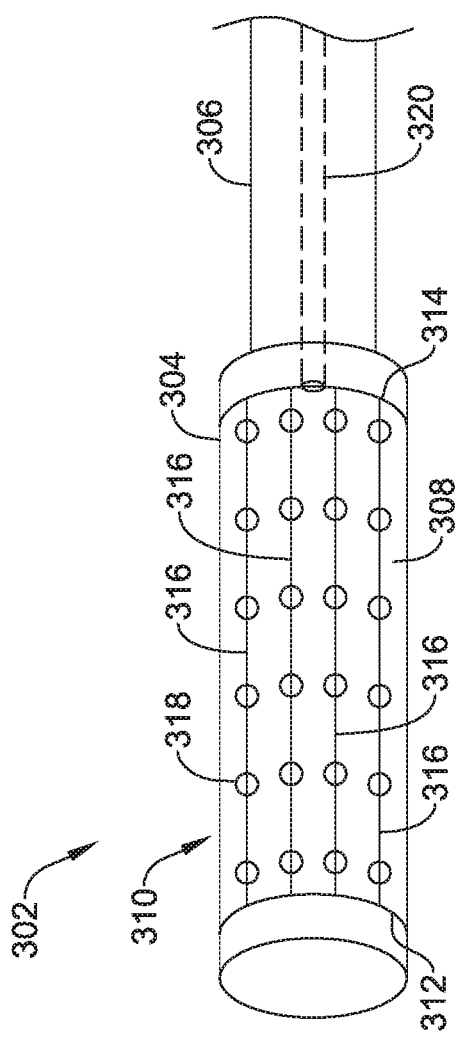

FIG. 12 shows another example. A delivery device 302, which may be considered as being an example of the delivery device 100, is shown with a device containment housing at 310, which may be considered as being an example of the device containment housing 108. The illustrative device containment housing 304 includes an electrode assembly 310 that includes a distal ring 312 and a proximal ring 314, with a plurality of electrode supports 316 extending between the distal ring 312 and the proximal ring 314. Each of the plurality of electrode supports 316 include a plurality of individually addressable electrodes 318. In some cases, the distal ring 312 is secured relative to the device containment housing 304 while the proximal ring 314 may be slidable relative to the device containment housing 304.

In some cases, a deployment member 320 may be operably coupled to the proximal ring 314 and extend proximally through the shaft 306 such that the proximal ring 314 may be moved forwards and backwards by pushing and pulling on the deployment member 320. In other cases, the distal ring 312 may be slidable, and the deployment member 320 may instead be operably coupled to the distal ring 312. In either case, in the deployed state, the individually addressable electrodes 318 may be used to capture intrinsic cardiac activity or to deliver therapeutic or non-therapeutic output. This may help determine a suitable implantation site for the LCP. Once a suitable implantation site has been determined, the deployment member 320 may be moved to retract the electrode supports 316, and the device containment housing 304 may be positioned over the suitable site and the LCP in the device containment housing 304 may be deployed and implanted at the site.

It will be appreciated that the electrode assembly 310 permits mapping of the endocardial surface. In some cases, this may be useful in determining or otherwise identifying intrinsic activation patterns. In some cases, mapping the endocardial surface may facilitate identification of scar tissue and possibly other damaged tissue, to be avoided when deploying the LCP 10. It will be appreciated that, in this example, while no sensors are shown as being part of the delivery device 302, one or more sensors such as pressure sensors, accelerometers and/or gyroscopes may be included as part of the delivery device 302 in order to gauge cardiac response to an applied stimulation via each of two or more of the individually addressable electrodes 318, for example.

Figure 13:
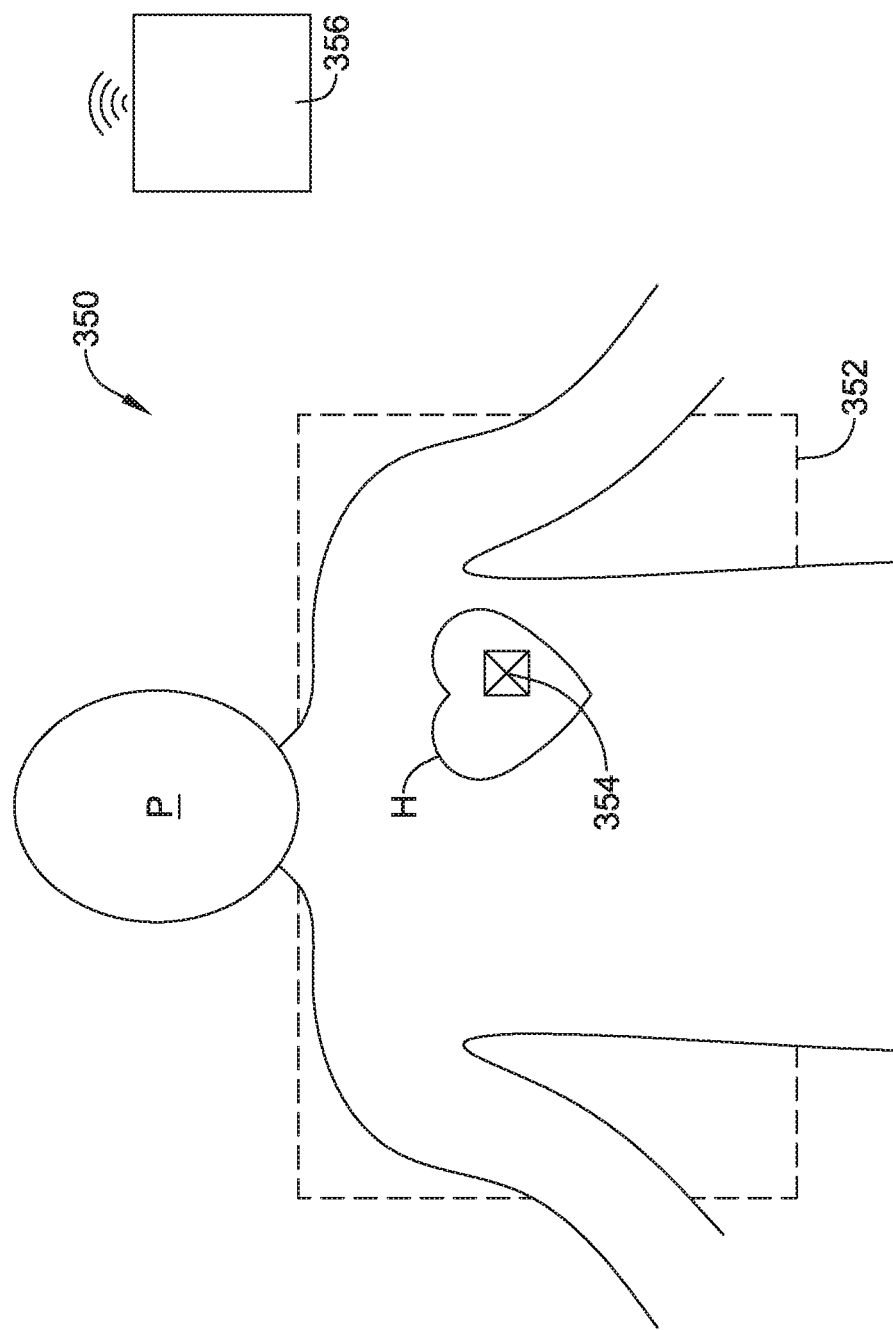
FIG. 13 shows an illustrative imaging system.

FIG. 13 schematically illustrates a system 350 in which a patient P, including a heart H, is placed in front of (or on top of) a magnetic field generator 352. In some cases, a device disposed within the heart H includes a magnetic tracking sensor and/or an impedance tracking sensor 354. In some cases, when the magnetic field generator 352 is generating a magnetic field, and the magnetic tracking sensor 354 within the device is turned on, the magnetic tracking sensor 354 is able to determine its location relative to the magnetic field lines, and to communicate this information for display on a monitor 356. When a current generator (not shown) provides current to the body (e.g. via two or more electrode patches), an impedance tracking sensor within the device may be able to determine its location relative to the electric field lines, and to communicate this information for display on a monitor 356. In some cases, both magnetic tracking and impedance tracking may be used to identify and track the location of the device. In some cases, the device including the magnetic tracking sensor and/or an impedance tracking sensor 354 may be a leadless cardiac pacemaker (LCP) or other intracardially implanted device, and the system 350 may provide an indication of the location of the device within the body. In some cases, the device including the magnetic tracking sensor and/or impedance tracking sensor 354 may instead be a delivery device, and the magnetic tracking sensor and/or an impedance tracking sensor 354 may provide an indication of the location of the delivery device. In some cases, the magnetic tracking sensor and/or impedance tracking sensor 354 may not only provide location (X,Y,Z), but may also provide pitch, yaw, velocity, acceleration, twist, and/or other parameters related to the device's position.

As illustrated, the system 350 may be a structure that the patient P lies on, or perhaps stands in front of. In some cases, it is contemplated that the magnetic field generator 352 may be incorporated into a wearable vest that may be used for ambulatory measurements. In some cases, information provided by the system 350 may be used to help guide initial implantation and to verify fixation of the device (such as the LCP 10). In some cases, the data provided may be used for determining rate response sensor calibration, as otherwise heart motion can interfere with detecting physical movement of the patient.

The delivery devices in the above examples, or components thereof, may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly (alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamides or ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTEL-LOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In some embodiments, portions or all of the delivery devices shown above, or components thereof, may be doped with, made of, or otherwise include a radiopaque material. Radiopaque materials are understood to be materials capable of producing a relatively bright image on a fluoroscopy screen or another imaging technique during a medical procedure. This relatively bright image may aid the user of the delivery device in determining its location. Some examples of radiopaque materials can include, but are not limited to, gold, platinum, palladium, tantalum, tungsten alloy, and the like. In some examples, a polymer material may be loaded with a radiopaque filler. Additionally, other radiopaque marker bands and/or coils may also be incorporated into the design of the delivery devices, or components thereof, to achieve the same result.

Figure 14:
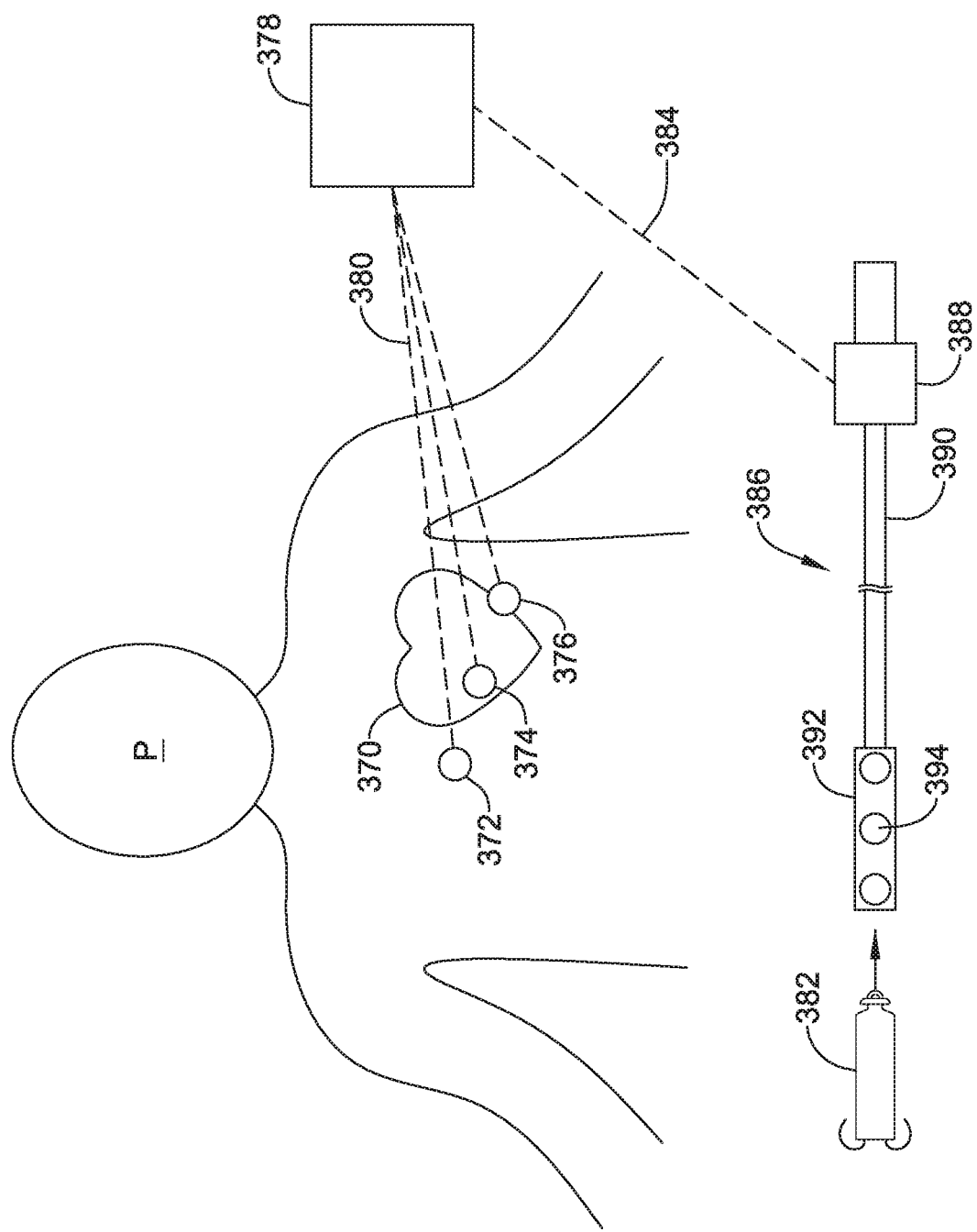
FIG. 14 shows an implantation system relative to a patient.

FIG. 14 shows an implantation guidance system relative to a patient. The patient P is shown with heart 370. One or more surface electrodes are placed as shown at 372, 374, 376, including a surface electrode 374 approximating Lead 2 of a standard EKG lead placement. Fewer or more surface electrodes may be provided at the shown or other locations.

An implant placement guidance device is shown at 378 and is communicatively coupled 380 to the surface electrodes 372, 374, 376. The coupling 380 may be by wireless communication or by attached wires, for example.

A device 382, shown as an LCP, is to be placed in the patient P in a chamber of the heart 370. The placement may be in the LV, or may be elsewhere including in the RV, an atrium, or in the coronary sinus. A delivery device is shown at 386 with a handle assembly 388, a distally extending shaft 390, and a device containment housing at 392 with a plurality of electrodes 394 on the containment housing 392. The delivery device 386, device containment housing 392, and electrodes 394 may be any of the above described illustrative examples.

The delivery device 386 is also coupled 384 to the implantation guidance system 378. The coupling 384 may again be wired or wireless, as desired. For example, the handle assembly 388 may include a wireless transceiver and corresponding circuitry to receive and pass along sensed signal data via wireless link to the implantation guidance system 378, if desired. During an implantation procedure, the guidance system 378 may be used to provide visual and/or audible indications related to the location of the device containment housing in the patient. In an example further illustrated below, the aim may be to identify a location which selected activation characteristics to facilitate measurement of the Q to LV activation for the heart 370 of the patient P.

In one example, the guidance system 378 may be integrated in a clinician programmer used to program the implantable device 382, as such are known in the art. An interface may be provided to the programmer to allow for the couplings 380, 384 via wired or wireless communication.

As an alternative to reuse of the clinician programmer, a dedicated device may be provided for an implant guidance system. FIG. 15 shows an illustrative implant placement guidance system. The system 400 may include operational circuitry, such as a dedicated circuit or set of circuits associated with a microcontroller, or a set of operational instructions to be operated on an overall microcontroller 408, to perform processing and comparison of signals received from a first input, Input A 410, and a second input, Input B 412. For example, input A 410 may be coupled to surface electrodes as shown in FIG. 14, in order to identify atrial activation and/or the Q-wave. Input B 412 may couple to the delivery device of FIG. 14 to receive signals captured by the electrodes on the device containment housing of the delivery device, in order to identify ventricular activation.

In this example, the aim is to find the timing between the Q-wave and ventricular activation, as indicated at 404. Block 404 may represent dedicated circuitry, or may be a set of operational instructions to be operated on an overall microcontroller 408. More particularly in this example, the aim is to identify a maximum Q-wave to ventricular activation interval. Such a maximum would indicate the latest intrinsic activation of the ventricle, which in this example is preferably the LV. Q-wave to LV activation intervals can provide useful information for optimizing cardiac resynchronization therapy (CRT).

The device 400 is shown as having a user interface 414, which may be or include a touch screen, a set of LED lights, and/or a speaker or the like. In an example, the user interface 414 may be the user interface of the clinician programmer, and the device 400 may swap the user interface 414 for a coupler to a USB port (or any other suitable port) of the clinician programmer, or a Bluetooth link to the clinician programmer, such that device 400 provides an interface between the clinician programmer and each of the surface electrodes and the delivery device.

Figure 16:
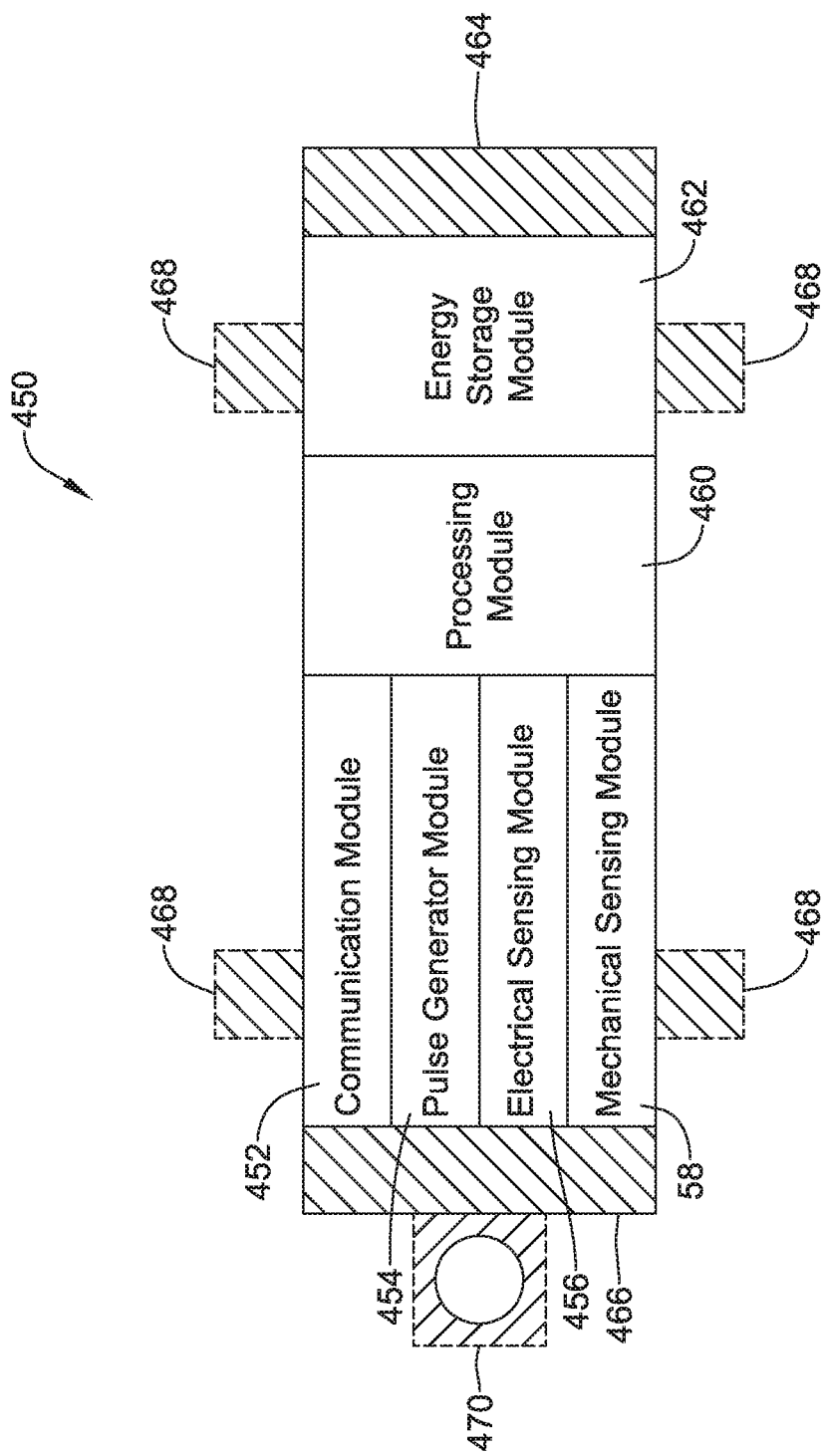
FIG. 16 shows an illustrative implantable leadless cardiac pacemaker with operational circuitry modules detailed.

FIG. 16 shows an illustrative implantable leadless cardiac pacemaker with operational circuitry modules detailed. The LCP 450 is shown as including several functional blocks including a communications module 452, a pulse generator module 454, an electrical sensing module 456, and a mechanical sensing module 458. In some examples, the electrical sensing module 456 and mechanical sensing module 458 may be configured to sense one or more biological signals for use in one or more of determining timing for CRT, identifying physiological conditions, such as those affecting the parasympathetic nervous system that may affect CRT timing needs, and/or for assessing CRT efficacy, as further described for example in U.S. Provisional Patent Application Ser. No. 62/424,582, titled LCP BASED PREDICTIVE TIMING FOR CARDIAC RESYNCHRONIZATION, and/or U.S. Provisional Patent Application Ser. No. 62/359,055, titled METHOD AND SYSTEM FOR DETERMINING AN ATRIAL CONTRACTION TIMING FIDUCIAL IN A LEADLESS CARDIAC PACEMAKER SYSTEM, the disclosures of which are incorporated herein by reference.

A processing module 460 may receive data from and generate commands for outputs by the other modules 452, 454, 456, 458. An energy storage module is highlighted at 462 and may take the form of a rechargeable or non-rechargeable battery, or a supercapacitor, for example and without limitation. If a rechargeable power source is provided, there may also be charging circuitry (not shown) to receive power from another implantable device or an external device. Various details and/or examples of internal circuitry, which may include a microprocessor or a state-machine architecture, are further discussed in US PG Patent Publications 20150360036, titled SYSTEMS AND METHODS FOR RATE RESPONSIVE PACING WITH A LEADLESS CARDIAC PACEMAKER, 20150224320, titled MULTI-CHAMBER LEADLESS PACEMAKER SYSTEM WITH INTER-DEVICE COMMUNICATION, 20160089539, titled REFRACTORY AND BLANKING INTERVALS IN THE CONTEXT OF MULTI-SITE LEFT VENTRICULAR PACING, and 20160059025, titled, MEDICAL DEVICE WITH TRIGGERED BLANKING PERIOD, as well as other patent publications.

The device is shown with a first end electrode at 464 and a second end electrode at 466. A retrieval feature is shown schematically at 470 and may be, for example, a short post with an opening therethrough to receive a retrieval hook, and/or may resemble several of the embodiments for an LCP 10 shown above. A number of tines 468 may extend from the device in several directions. The tines 468 may be used to secure the device in place within a heart chamber. The tines 468 may instead resemble attachment features shown above. An attachment structure may instead take the form of a helical screw, if desired. In some examples, tines 468 are used as the only attachment features. As noted above, delivery, tissue attachment and retrieval features may be included in the LCP including those features shown in US PG Patent Publications 20150051610, and/or 20150025612, titled SYSTEM AND METHODS FOR CHRONIC FIXATION OF MEDICAL DEVICES, for example.

In an illustrative example, consistent with the methods discussed below, once the LCP 450 is implanted, the electrical sensing module 456 may be used to detect, locally, an R-wave. For example, if the LCP 450 is in or on the left ventricle, a point in time of activation of the portion of the cardiac tissue can be determined by monitoring for the electrical peak with the electrical sensing module 456, using one or more electrodes 464, 466, or even using the tines 468 if the tines are coupled electrically to the electrical sensing module 456. The processing module 460 may observe an output of the electrical sensing module 456 to identify the R-wave. The R-wave may be verified by the processing module 460 by checking for a mechanical signal from the mechanical sensing module 458 indicating motion corresponding to the identified R-wave, if desired.

In some examples, the processing module 460 may then use the communication module to issue a message to another device to indicate the timing of the R-wave which may then be used to determine various useful information including, for example, the Q-wave to LV R-wave interval. In some other examples, the processing module 460 may receive information that can be integrated with the R-wave detection time to determine various useful information including, for example, the Q-wave to LV R-wave interval. The LCP 450 may itself make adjustments to therapy timing or other characteristics of therapy using data or commands communicated to it via the communications module 452 and/or as a result of its own, internal analysis.

In some examples, an optimal atrial-ventricular delay (AVD) period may be determined by testing plural AVD intervals while observing the peak change in pressure within the LV. Relatively higher pressure change in the LV may be indicative of improved synchrony in the cardiac contraction. For patients with a greater degree of electrical dyssynchrony, the optimal AVD may be shorter (for example, in the range of 30 to 40 percent of the intrinsic A to RV (ARV) interval)

than for patients showing less dyssynchrony, for whom an AVD in the range of 70-80 percent of the intrinsic ARV interval may be more optimal. Some discussion of such relationships may be found in Auricchio, et al., EFFECT OF PACING CHAMBER AND ATRIOVENTRICULAR DELAY ON ACUTE SYSTOLIC FUNCTION OF PACED PATIENTS WITH CONGESTIVE HEART FAILURE. Circulation 1999; 99:2993-3001.

Figure 17:
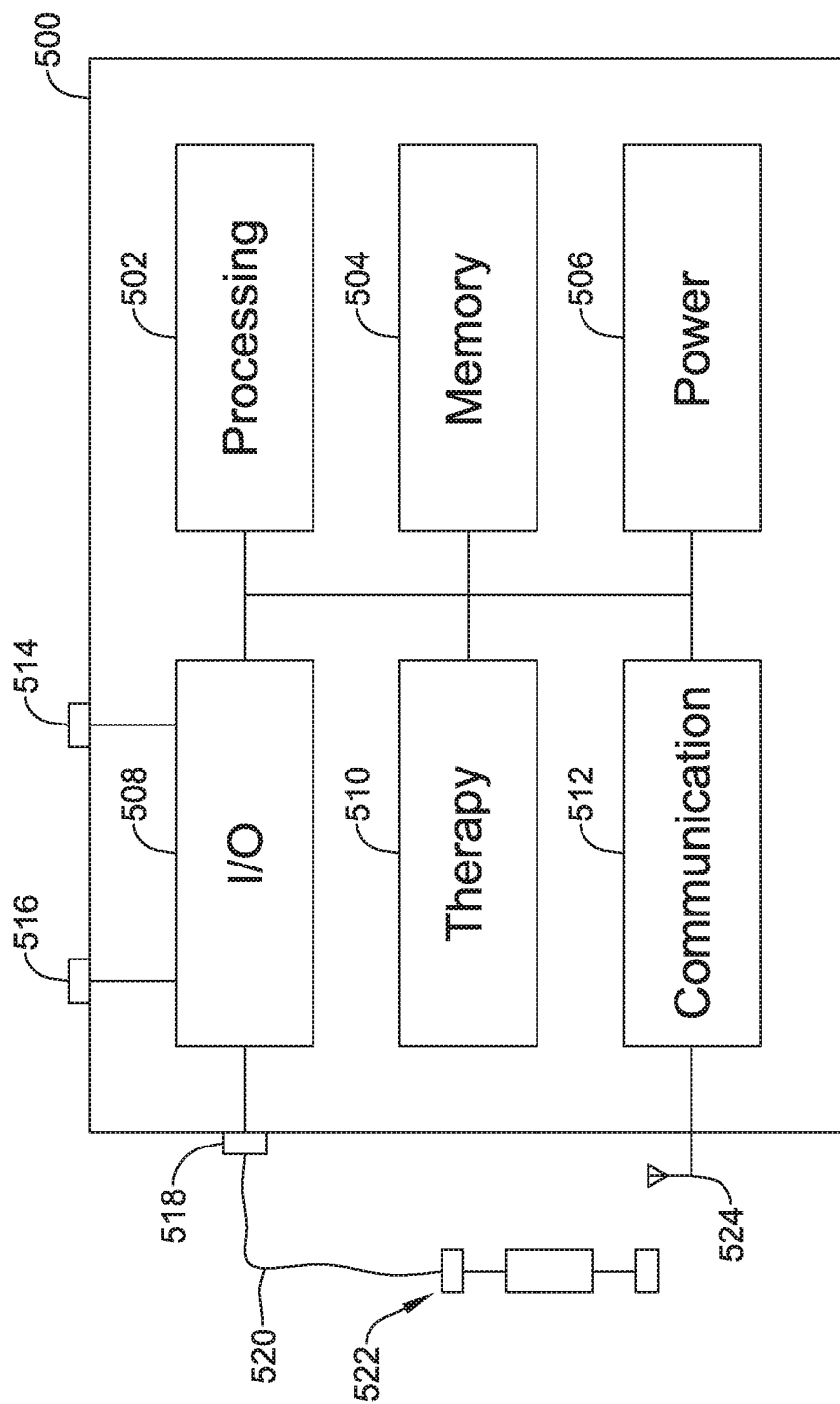
FIG. 17 shows an illustrative implantable medical device for use with an implantable pacemaker in some examples.

FIG. 17 shows an illustrative implantable medical device for use with a leadless cardiac pacemaker in some examples. The illustration indicates various functional blocks within a device 500, including a processing block 502, memory 504, power supply 506, input/output circuitry 508, therapy circuitry 510, and communication circuitry 512. These functional blocks make up at least some of the operational circuitry of the device. The I/O circuitry 508 can be coupled to one or more electrodes 514, 516 on the housing of the device 500, and may also couple via a header 518 for attachment to one or more leads 520 having additional electrodes 522.

The processing block 502 will generally control operations in the device 500 and may include a microprocessor or microcontroller and/or other circuitry and logic suitable to its purpose. A state machine may be included. Processing block 502 may include dedicated circuits or logic for device functions such as converting analog signals to digital data, processing digital signals, detecting events in a biological signal, etc. The memory block may include RAM, ROM, flash and/or other memory circuits for storing device parameters, programming code, and data related to the use, status, and history of the device 500. The power supply 506 typically includes one to several batteries, which may or may not be rechargeable depending on the device 500. For rechargeable systems there would additionally be charging circuitry for the battery (not shown) including for example a coil for receiving energy and regulating and rectification circuitry to provide received energy to a rechargeable battery or supercapacitor.

The I/O circuitry 508 may include various switches or multiplexors for selecting inputs and outputs for use. I/O circuitry 508 may also include filtering circuitry and amplifiers for pre-processing input signals. In some applications the I/O circuitry will include an H-Bridge to facilitate high power outputs, though other circuit designs may also be used. Therapy block 510 may include capacitors and charging circuits, modulators, and frequency generators for providing electrical outputs. A monitoring device may omit the therapy block 510 and may have a simplified I/O circuitry used simply to capture electrical or other signals such as chemical or motion signals.

The communication circuitry 512 may be coupled to an antenna 524 for radio communication (such as Medradio, ISM, Bluetooth, or other radiofrequency protocol/band), or alternatively to a coil for inductive communication, and/or may couple via the I/O circuitry 508 to a combination of electrodes 514, 516, 522, for conducted communication. Communication circuitry 512 may include a frequency generator, oscillator and/or mixer for creating output signals to transmit via the antenna 524. Some devices 500 may include a separate or even off-the shelf chip for the communications circuitry 512, for example. For devices using an inductive communication output, an inductive coil may be included. Devices may use optical or acoustic communication, and suitable circuits, transducers, generators and receivers may be included for these modes of communication as well or instead of those discussed above.

As those skilled in the art will understand, additional circuits may be provided beyond those shown in FIG. 17. For example, some devices 500 may include a Reed switch, Hall Effect device, or other magnetically reactive element to facilitate magnet wakeup, reset, or therapy inhibition of the device by a user, or to enable an MRI protection mode. A device lacking a lead may have plural electrodes on the housing thereof, as indicated at 514, 516, but may omit the header 518 for coupling to lead 520.

A device as in FIG. 17 may be embodied as a subcutaneous implantable defibrillator, such the S-ICD System from Boston Scientific. Alternatively a device 500 may be embodied as an implantable defibrillator and/or pacemaker as in US PG Patent Application Pub. No. 2017-0021159, titled SUBSTERNAL PLACEMENT OF A PACING OR DEFIBRILLATING ELECTRODE, the disclosure of which is incorporated herein by reference. Another alternative placement is shown in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference. Still further, a device 500, omitting the therapy circuitry 510 if desired, may be embodied as an implantable cardiac monitoring system.

In an illustrative example, consistent with the methods discussed below, the device as in FIG. 17 may use the I/O module 508 to capture a cardiac signal or signals. R-waves may be detected by, for example, comparing the sensed signal to a detection threshold, such as shown in U.S. Pat. No. 8,565,878. Each R-wave corresponds to a cardiac cycle, within which there will generally be P, Q, S and T waves, according to widely used convention. The timing of an atrial event, such as the P-wave, and or the septal Q-wave, may be determined from an individual cardiac cycle using analysis of morphology and/or turning points, or by assessment of a composite of several cardiac cycles. For example, the Q-wave may be identified using identification of a deflection following the P-wave but prior to the R-wave. For example, the P-wave and Q-wave would generally be of opposing polarity, and the Q-wave will be the first deflection after the P-wave, but prior to the much larger R-wave deflection. For some patients, the Q-wave itself may be missing (based for example on the positioning of the sensing electrodes making detection difficult or impossible); for such patients, a first deflection of preset polarity after completion of the P-wave may be used.

Figure 18:
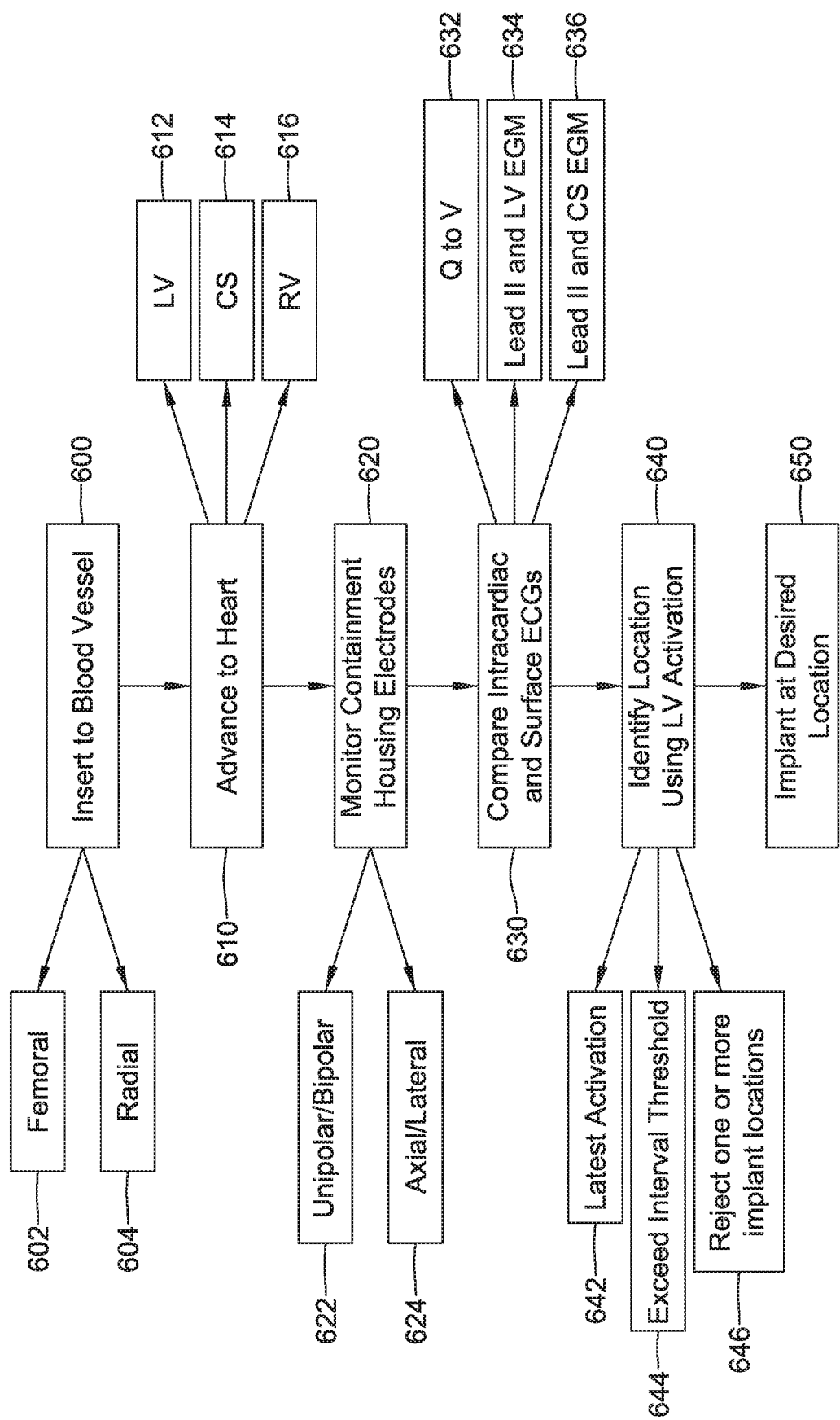
FIGS. 18-20 show illustrative methods in block diagram form.
Figure 19:
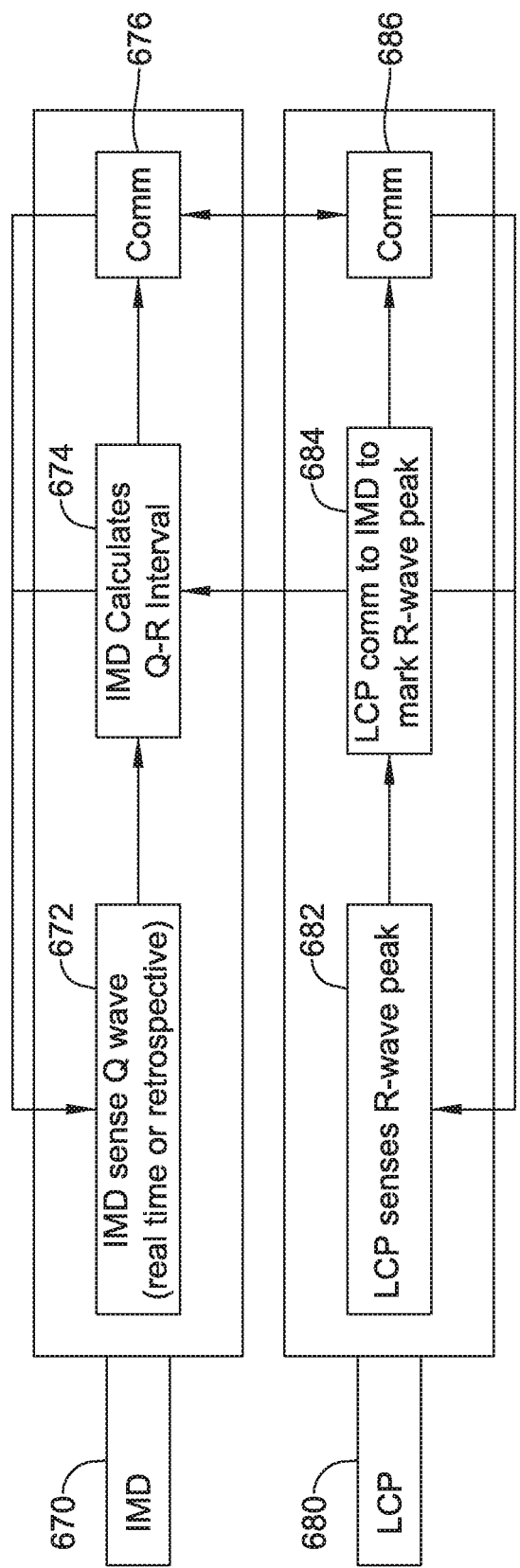
Figure 20:
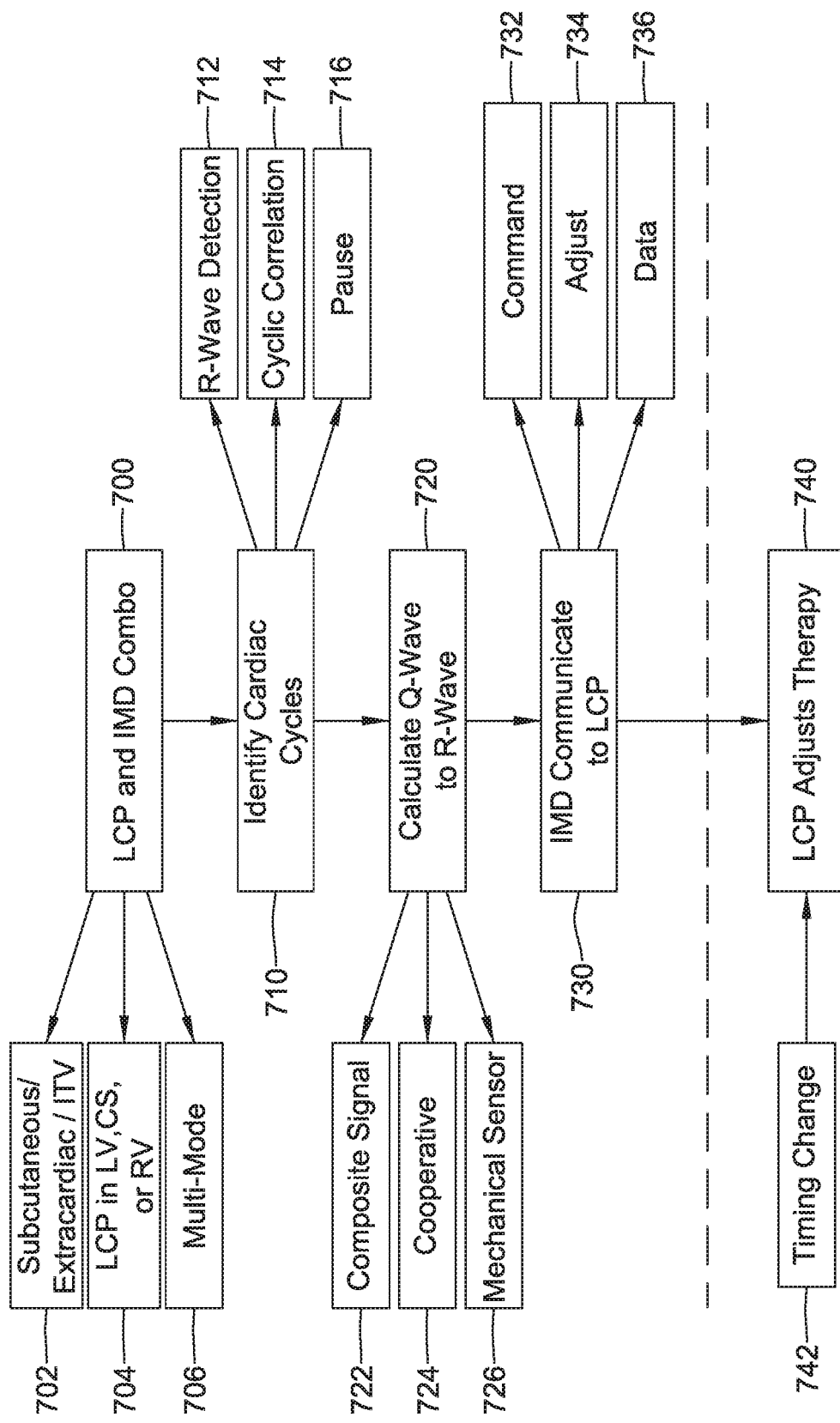

FIGS. 18-20 show illustrative methods in block diagram form. FIG. 18 illustrates a method for implantation of a device such as an LCP. The LCP may be inserted on a delivery device as shown above. The LCP is first inserted in a blood vessel, as indicated at 600. This step 600 may include, for example, standard venous access techniques (Seldinger, cut-down, etc.) known in the art for accessing for example a femoral vein 602 or even a radial vein 604, or some other location such as the subclavian vein or axillary vein. For endocardial LV implantation, a retrograde aortic approach may be used in which the access would be the femoral artery or another peripheral artery, threading the implantation device up through the arterial pathways to then enter the heart in retrograde manner from the aorta.

The LCP is advanced to the heart of the patient, as indicated at 610. Any suitable chamber or location may be used, including in several examples the left ventricle (LV) as indicated at 612. In other examples, the coronary sinus (CS) 614 or right ventricle (RV) may be selected.

Once the LCP is in the desired chamber of the heart—that is, generally near where it is to be implanted but not yet attached to the myocardium, the method comprises monitoring containment housing electrodes as indicated at 620. In this example, a delivery device as shown above having a containment housing may be used. Moreover, the containment housing may have electrodes on the sides or tip thereof as shown in FIGS. 6-12, above. Such electrodes on the device containment housing may be used in unipolar or bipolar sensing approaches as indicated at 622. For example, a unipolar sensing approach would use one electrode on the containment housing as one pole of a sensing pair, and a distant electrode such as an electrode patch, disk or plate on the skin of the patient. A bipolar sensing approach would use two electrodes on a distal portion of the delivery device, such as two electrodes on the containment housing, as opposing poles of the sensing pair. A unipolar approach may provide a greater signal amplitude but may also be more prone to noise and lower sensitivity to onset, while the bipolar approach may give a very sharp signal onset but may be inconsistent insofar as the sensed signal may vary more widely with contact and motion within the heart of the cardiac tissue as well as the electrodes on the device containment housing. The device containment housing may have electrodes at the axial tip (FIGS. 11 and 12) and/or on the lateral sides thereof (FIGS. 6-10 and 12), as indicated at 624.

Next, as indicated at 630, the intracardiac sensed signals are compared to the surface electrocardiograms. For example, using a system as shown above in FIG. 14, the intracardiac signals are captured using the delivery device (in unipolar or bipolar fashion, as noted at 622), and the surface signals are captured using a set of surface electrodes. These are compared by identifying the Q-wave timing from the surface electrodes and identifying a ventricular activation signal from the intracardiac electrodes, as indicated at 632. The "v" signal in 632 may be captured, for example, from the LV, RV, CS, or other location as descried above, with the signal being dependent upon the location of the intracardiac sense electrodes. For example, this step may be used to generate an interval between the Q-wave as detected with Lead II of a standard ECG and the R-wave sensed with the delivery device which may be in the LV, as indicated at 634. In another example, this step may be used to generate an interval between the Q-wave as detected with Lead II of a standard ECG and the R-wave sensed using electrodes of a delivery device in the CS, as indicated at 636.

A location for LCP implantation is identified as indicated at 640. This may be done by testing a number of locations and determining that of the latest ventricular activation, as indicated at 642. In another example, testing may be performed to identify a location that at least exceeds a predetermined interval from Q-wave (or other supraventricular timing fiducial) to local ventricular activation, as indicated at 644. For example, a position with a Q-LV interval of at least in the range of 150 to 200 milliseconds may be sought out, such as for example, an interval of 180 milliseconds. In some examples, one or more implant position may be rejected as indicated at 646 by rejecting those positions having a Q-LV interval of below a set threshold, such as a Q-LV interval of 120 to 160 milliseconds. The numbers provided are merely examples and may be adjusted for a given patient or implementation. If other AV delay measures are used, these thresholds may be adjusted. In another example, a patient who is receiving a system will have a known, measured QRS width, which may be used in part to determine whether the patient is indicated to receive an implantable cardiac resynchronization system in the first place. For a patient having a known, measured QRS width, an acceptable (block 644) or unacceptable (block 646) Q-LV interval may be calculated as a percentage of the QRS width. For example, a Q-LV interval acceptance criteria may be set at 75 to 100 percent of the known QRS width for use at block 644. In another example, Q-LV minimum acceptance criteria—used to reject implant locations at 646, may be set to about 50 to about 80 percent of the known QRS width. Again, the numerical ranges are exemplary and may be modified for other configurations and measures.

A mapping tool, as discussed above relative to FIG. 13, may be used so that plural tests can be performed to find the latest activation, which may not be apparent until the delivery device has been moved away from the desired location, with the mapping tool used to allow the physician to readily return the device to the desired location.

Finally, the LCP can be implanted at the desired location, as indicated at 650. Implantation may be achieved as shown above, with the LCP being pushed out of the device containment housing while attachment features are activated to secure the LCP to the heart wall.

FIG. 19 illustrates another method. Unlike FIG. 18, which is directed at implantation, FIG. 19 is directed to monitoring performance of the implanted system and making adjustments to the therapy while it operates. An IMD, such as the IMD of FIG. 17 operates as shown at 670. The IMD may be, for example, a cardiac monitoring apparatus, or a therapy delivery device such as an implantable defibrillator in a subcutaneous-only lead configuration, a substernal (mediastinal) lead configuration, or a configuration with one or more leads in the internal thoracic veins and/or intercostal veins, as described in references cited above.

An LCP, such as the LCP shown in FIG. 16 and elsewhere described above, has operations as shown at 680. The IMD and LCP may communicate with one another using any suitable methods and circuitry such as those using inductive, conductive, optical, sonic, or radiofrequency communication.

In the method, the IMD is adapted to sense the Q-wave, as indicated at 672. This step 672 may be done in real-time for each cardiac cycle, or may be performed using a retrospective analysis in which plural cardiac cycles are analyzed together in a composite signal to identify Q-wave timing. The LCP also performs sensing, in this example, to identify the R-wave peak, as indicated at 682. The R-wave peak at 682 may be specific to the LCP location and therefore may be an LV R-wave peak, a CS R-wave peak, or an RV R-wave peak. Rather than a peak, onset of the R-wave may be determined in other examples, or both peak/onset and R-wave width may be calculated, as desired.

The LCP communicates to the IMD as indicated to 684 to mark the R-wave peak. This may be done in real time, or may rely on time stamps and system clock coordination to allow the IMD to determine when, relative to the Q-wave detected by the IMD, the R-wave occurred. The IMD then determines the Q-R Interval, as indicated at 674. The interval at 674 may be the Q wave to LV R-wave, or Q-wave to RV R-wave, or Q-wave to CS R-wave, in various examples. Optionally the devices can communicate with one another at 676/686 to adjust pacing therapy timing for the LCP as needed. For example, if the Q-wave to LV R-wave is too long, relative to a desired interval, the LCP may adjust the timing it uses for pace therapy delivery if the LCP determines such timing to an internal clock or interval. For example, as shown in U.S. Provisional Patent Application Ser. No. 62/378,880, titled INTEGRATED MULTI-DEVICE CARDIAC RESYNCHRONIZATION THERAPY USING P-WAVE TO PACE TIMING, and/or U.S. Provisional Patent Application Ser. No. 62/378,866, titled CARDIAC RESYNCHRONIZATION USING FUSION PROMOTION FOR TIMING MANAGEMENT, the LCP may deliver CRT pacing at set intervals relative to a prior LCP pace delivery with updates from the IMD; for such a system, the LCP may adjust its timing in response to communications from by the IMD. In another example, as shown in U.S. Provisional Patent Application Ser. No. 62/355,121, titled CARDIAC THERAPY SYSTEM USING SUBCUTANEOUSLY SENSED P-WAVES FOR RESYNCHRONIZATION PACING MANAGEMENT, if the IMD commands pace delivery by the LCP, then the IMD may adjust the timing it uses for such commands. The method can then return to blocks 672/682.

The updates to LCP therapy shown in FIG. 19 may be performed on an ongoing basis or at intervals or in response to detected events. For example, if the patient changes posture (which the IMD or LCP may detect using a posture/position sensor or by analysis of changes to the sensed cardiac signal), the method may be performed to optimize therapy delivery for a new posture. If the patient's activity level changes, this may also trigger the method to be performed.

FIG. 20 shows another example for an LCP and IMD combination system. An LCP and an IMD are both implanted in a patient, as indicated at 700. The 1 MB may be, for example, a monitoring device or a therapy device having a subcutaneous-only implant location, an extracardiac or substernal/mediastinal lead configuration, or a device with a lead in the internal thoracic vein (ITV) and/or an intercostal vein, as indicated at 702. The LCP may be implanted in the LV, CS, or RV, as indicated at 704.

A system may be a multi-mode system, as indicated at 706, where the IMD is adapted for use with an LCP implanted in any of the LV, CS, CS tributary, ECV, or RV locations, if desired. For example, the 1 MB may comprise stored operational instructions in a memory for execution by a controller or processor such as a microcontroller providing selectable modes for operation with an LCP in the LV or an LCP in the CS. Cardiac cycles are identified as indicated at 710 by the 1 MB and LCP. R-wave detection may be used as indicated at 712 in the IMD and the LCP. If desired, cyclic correlation may be used as indicated at 714. Cyclic correlation may be used to identify an atrial event by comparing an atrial event template to incoming cardiac signals, and may further be used to detect features of the P-wave, as described in U.S. Provisional Patent Application Ser. No. 62/355,121, titled CARDIAC THERAPY SYSTEM USING SUBCUTANEOUSLY SENSED P-WAVES FOR RESYNCHRONIZATION PACING MANAGEMENT. Cyclic correlation may be an adjunct to R-wave detection 712 to identify the atrial events in a window prior to an R-wave using a predictive analysis that predicts when a P-wave will occur after a preceding cardiac cycle is completed, or using a retrospective analysis to find the P-wave that precedes a detected R-wave. Such analysis can be used to identify the Q-wave as sensed by the IMD. In some examples, a pause 716 in a therapy regimen provided by the LCP may be used to provide an opportunity to capture intrinsic cardiac activity to obtain a measurement of the intrinsic Q-wave to R-wave interval in later blocks. For example, a number of pace therapies (five to five hundred cycles, for example, or more or less), duration (five seconds to an hour, for example, or more or less) of pacing therapy may pass between pauses of one to ten cardiac cycles to facilitate review of intrinsic cardiac state.

Next, as indicated at 720, the Q-wave to R-wave interval is calculated. The interval may be the Q-wave as detected by the IMD to an R-wave as detected by the LCP in the LV, RV or CS. This analysis at 720 may use a composite signal, as indicated at 722 to assist in finding the Q-wave. The analysis at 720 may be cooperative 724 in that the R-wave is detected by a first device, the LCP, and the Q-wave is detected by a second device, the 1 MB. The analysis at 724 may further take into account mechanical sensing inputs to modify the target Q-wave to R-wave interval by for example, shortening the Q-wave to R-wave interval in the event that a mechanical patient activity sensor detects elevated patient activity. Alternatively, the Q-wave to R-wave interval may be extended or shortened in response to patient posture, such as by extending the Q-wave to R-wave interval if the patient is laying down, indicating a period of rest potentially. It is known, for example, to use an accelerometer to detect patient posture or movement.

As indicated at 730 the 1 MB, in this example, then communicates to the LCP in order to optimize LCP therapy delivery using the Q-wave to R-wave interval calculated at 720. For example, the IMD may command pace therapy delivery on a pace by pace basis, as indicated at 732, with the commands issued using a timing determined using the Q-wave to R-wave interval from block 720. The 1 MB may instead communicate an adjustment to the LCP for the LCP to make, as indicated at 734. Finally, the IMD may simply communicate data to the LCP to allow the LCP to determine which adjustments, if any, are to be made.

In response to the communication at 730, the LCP adjusts its therapy delivery, particularly if the IMD communicates an adjustment 734 or communicates data 736 allowing the LCP to make its own determination of an adjustment. For example, the LCP may adjust the timing of pace therapy delivery, as indicated at 742.

Figure 21:
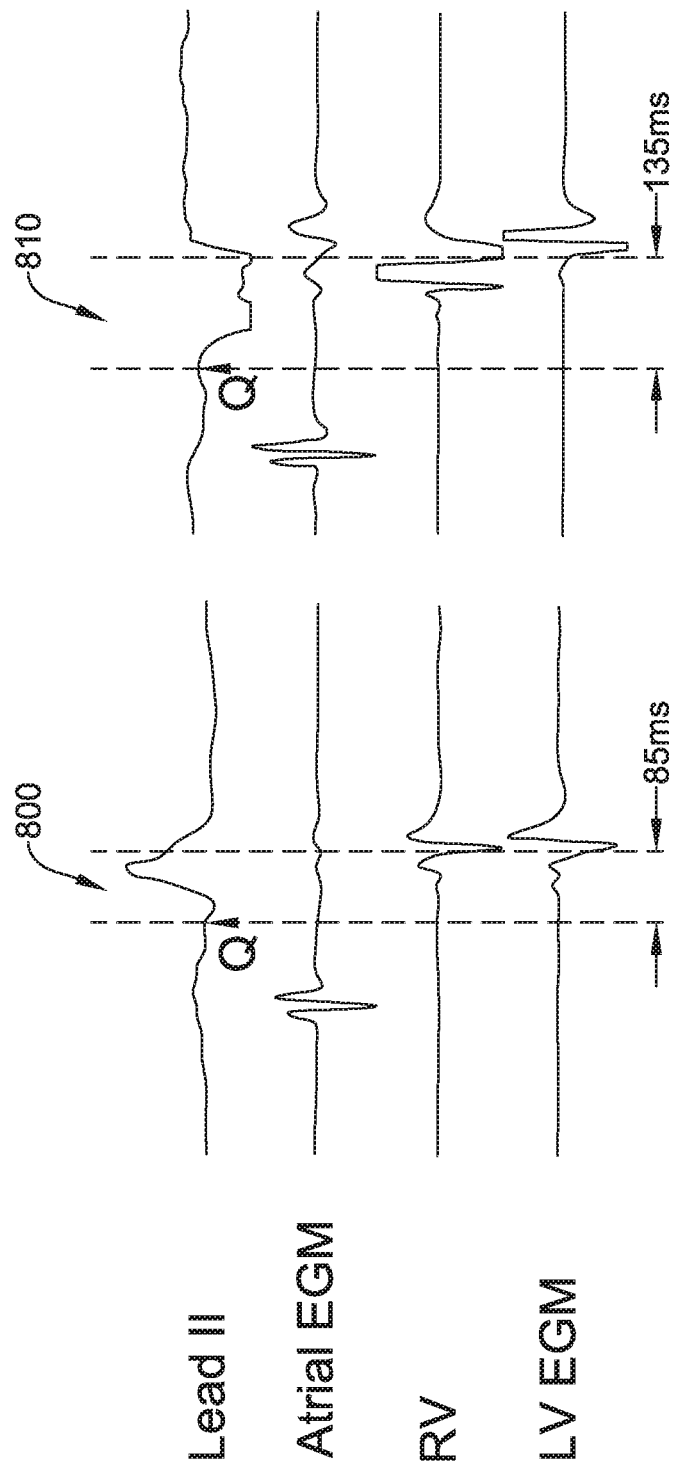
FIG. 21 shows cardiac signals as taken from several views for an illustrative embodiment.

FIG. 21 illustrates the effect of such analysis on patients with different cardiac signal characteristics. Cardiac signal features for a first patient having lesser dyssynchrony are illustrated at 800. The cardiac signal captured using Lead II of a standard ECG is shown with the Q-wave highlighted. For this patient, the atrial EGM shows atrial depolarization prior to the Q-wave in Lead II, and the RV depolarization occurs shortly thereafter. The LV EGM shows depolarization largely synchronized with the RV, yielding a Q-wave to LV interval of about 85 milliseconds. Thus patient 800 has a total QRS width of 120 milliseconds or so, showing less dyssynchrony.

The signal is quite different for the patient shown at 810. Here, again, Lead II shows the Q-wave after the Atrial EGM shows atrial depolarization. Lead II shows an inverted cycle subsequent to the Q-wave, when compared to the first patient, indicative of a lack of synchronization, which is better understood with the separate electrograms for the RV and LV, below. Here, the RV depolarization begins well ahead of the LV depolarization, creating a Q-wave to LV onset delay that is 135 milliseconds. A system which can determine this interval is able to determine further that the LV pacing regimen can be enhanced by delivering the LV pace earlier relative to the interval between atrial activation and RV activation, to bring the LV depolarization into better alignment with the RV activation.

A set of measures as shown in FIG. 21 may be useful in an immediate sense to diagnose a patient's present state. In some examples, data may be trended as well. For example, monitoring intrinsic Q-wave activation to ventricular depolarization times on an hourly, daily, and/or weekly basis (or at other interval) may be useful to observe a patient's heart failure or synchronization state over time. Taking the QLV interval (the interval from Q-wave onset to, for example, LV depolarization at a selected location in the LV), an increase in that interval would indicate worsening electrical synchrony, which may be associated with worsened outcomes for CRT. Changes exceeding a set threshold, or measures outside of set boundaries, may trigger alerts or alarms to suggest that a patient ought to visit his or her physician. The goal would be to allow intervention while the patient is outwardly asymptomatic, rather than waiting for onset of symptoms that could lead to hospitalization.

For example, a change of more than, for example, 5% to 20%, or 10% in another example, of the Q-wave to R-wave activation interval or AV activation interval may be sufficient to cause an alert to the patient or to a physician via a remote monitoring network. Rather than a percentage, an absolute change may be tracked for example, 10 to 30 milliseconds of change.

In another example, an absolute threshold for the interval of interest may be set, in the range of, for example, 75 to 110 milliseconds, or in still a further example, at about 90 milliseconds, for an epicardial approach using a device implanted in the CS or tributary thereto. For endocardial implant with an LCP, the range may be somewhat lower, for example, about 60 to about 100 milliseconds, or in a still further example, at about 70 to 80 milliseconds, for issuing an alert. An alert may be set to a first level, with an alarm at a second level, to facilitate multiple layers of response—an alert may be issued to a patient using a patient programmer or home monitor, and an alarm may be issued via a patient programmer or home monitor using cellular or internet communications to contact a physician, clinic, or device manufacturer, or other interested party. For example, an absolute threshold for the QRV interval may be set to 80 milliseconds for an LCP-based system for alert purposes, and a trend or delta threshold may be set for alarm purposes at 15% from a prior baseline for the QRV interval. Other numerical boundaries may be used and those provided are merely for ease of explanation.

A trend may be monitored and extrapolated to allow an alert or alarm to be generated if extrapolation (such as line-fitting of the trend) suggests that the patient will soon cross an alert or alarm threshold. In still another example, variability, rather than a trend, may be monitored, with high variability in measurements over time suggestive of a poorly treated condition such as medication taken at too long an interval, or changes in physiology suggesting that a patient may be coached on moderation of activity and/or nutrition.

In another example, a trending mode may be effected to create trends over a shorter period of time, such as by delivering CRT pacing therapy for a selected quantity of beats (10 to 100, for example) followed by a small number of intrinsic beats to allow measurement of intrinsic intervals such as Q-wave activation to ventricular depolarization over the course of a day. The shorter term trending mode may be used to determine effects of medicine, diet, exercise or other events in a patient's day on cardiac synchrony to aid in diagnosis and/or treatment of the patient's condition.

FURTHER NOTES & EXAMPLE EMBODIMENTS

A first illustrative and non-limiting embodiment takes the form of an implant guidance system for implanting a leadless cardiac pacemaker (LCP) in or adjacent to the heart of a patient, the system comprising: an LCP delivery system for implanting an LCP having a proximal end with a handle for manipulating a position of the LCP in a patient and a distal end having a means for holding the LCP during an implantation procedure (a means for holding may be a containment housing 108 (FIGS. 2-5), 204 (FIG. 6), 228 (FIG. 7), 252 (FIG. 8), 272 (FIG. 9), 282 (FIG. 10), 292 (FIG. 11), 304 (FIG. 12), or 392 (FIG. 14), the distal end of the LCP delivery system comprising one or more electrodes for capturing cardiac signals during implantation of the LCP (such an LCP delivery system is shown, for example, in FIGS. 3-12, with additional details in FIG. 14; electrodes are shown at or near the distal end in several of those examples); and a guidance device (FIG. 15, 400) comprising a first input means (FIG. 15, 410) to receive cardiac signals from a plurality of surface electrodes on a patient and a second input means (FIG. 15, 412) to receive cardiac signals from the LCP delivery system, a user interface (FIG. 15, 414) having at least one of an audible or visual output, and a processor (FIG. 15, 408) comprising a timing means (FIG. 15, at 404; block 404 may represent dedicated circuitry, an application specific integrated circuit, and/or stored instruction sets in a memory for execution by a controller or processor, or operations for an operating state of a state machine, or the like, configured to perform the function recited) to determine timing between a signal obtained from the first input means representing an atrial timing fiducial and a signal obtained from the second input means representing a ventricular timing fiducial to determine an AV timing interval when the LCP delivery system is in at least a first position, and alert means (FIG. 15, at block 406; block 406 represent dedicated circuitry, an application specific integrated circuit, and/or stored instruction sets in a memory for execution by a controller or processor, or operations for an operating state of a state machine, or the like, configured to perform the function recited) for using the user interface to alert a user as to whether the AV timing interval suggests at least one of a suitable or unsuitable implant location for the LCP. FIG. 18 shows an example of a process flow for a device as indicated in this first illustrative example, and the description thereof provides additional exemplary details.

A second illustrative non-limiting embodiment takes the form of an implant guidance system as in the first illustrative non-limiting embodiment, wherein the atrial timing fiducial is a Q-wave, and the ventricular timing fiducial is a locally sensed ventricular activation.

A third illustrative non-limiting embodiment takes the form of an implant guidance system as in the first illustrative non-limiting embodiment, wherein the timing means is configured to calculate a plurality of AV timing intervals as the LCP delivery system is manipulated by a user to a plurality of positions, and the alert means includes peak identifier means to identify a peak AV timing interval of the plurality of AV timing intervals to trigger an alert to the user, the peak AV timing interval being associated with a suitable implant location for the LCP.

A fourth illustrative non-limiting embodiment takes the form of an implant guidance system as in the first illustrative non-limiting embodiment, wherein the alert means comprises width means to compare the AV timing interval to a known QRS width for the patient to trigger an alert to the user.

A fifth illustrative non-limiting embodiment takes the form of an implant guidance system as in any of the first to fourth illustrative non-limiting embodiments, wherein the LCP delivery system comprises a containment housing for the LCP, the containment housing has a plurality of electrodes thereon (such containment housings are shown above in any of FIGS. 3-12 and 14), and the LCP delivery system includes means for electrically conducting signal from the at least two electrodes to the handle thereof (FIGS. 6-8 each illustrate coupling of conductive wires to the electrodes disposed relative to a containment housing).

A sixth illustrative non-limiting embodiment takes the form of an implant guidance system as in the fifth illustrative non-limiting embodiment, wherein the LCP delivery system containment housing includes a forward end comprising at least one electrode thereon for sensing cardiac signals during implantation of the LCP (such a design is shown in FIG. 11, which electrodes on the forward end or distal tip 294, as shown at 298, 300).

A seventh illustrative non-limiting embodiment takes the form of an implant guidance system as in the fifth illustrative non-limiting embodiment, wherein the LCP delivery system containment housing has a forward end with an opening for releasing the LCP therethrough and sidewalls for containing the LCP during implantation, wherein the sidewalls comprise at least one electrode thereon for sensing cardiac signals during implantation of the LCP.

An eighth illustrative non-limiting embodiment takes the form of an implantable medical device (IMD) configured for use with a leadless cardiac pacemaker (LCP) implanted in the left ventricle or coronary sinus of a patient and configured to communicate to and/or from the LCP while implanted using wireless or conducted communication, the IMD comprising: a plurality of electrodes for sensing cardiac electrical activity (FIG. 17, at 514, 516, 522, for example); cycle means for analyzing the sensed cardiac electrical activity from the plurality of electrodes and identifying cardiac cycles therein (cycle means may take the form of a dedicated circuit or stored instruction sets for performing cardiac cycle detection, sometimes driven by R-wave detection, to be performed by a processing block 502 in FIG. 17; cycle detection is part of the IMD activity at 672 in FIG. 19, and is also at block 710 in FIG. 20); AV interval means to calculate a measure of Q-wave to left ventricle (LV) R-wave peak timing for one or more cardiac cycles (such AV interval means may take the form of a dedicated circuit or stored instruction set for performing calculations to determine the AV interval using the recited inputs, as illustrated for example at block 674 of FIG. 19 and block 720 of FIG. 20); IMD communication means to communicate with the LCP (such communication means, which may use RF or inductive telemetry and/or conducted communication, are shown as part of an IMD at block 512 of FIG. 17); and adjustment means to determine that the LCP should adjust a therapy regimen using at least the measure of Q-wave to LV R-wave peak timing (such adjustment means may take the form of a dedicated circuit and/or stored instruction set for execution by a controller or processor for determining an adjustment as indicated at lock 734 of FIG. 20), wherein the adjustment means is configured to use the communication means to communicate to the LCP in response to a determination that the LCP should adjust the therapy regimen (as indicated in FIG. 19, communication is performed at locks 676, 686 between the devices once the interval is known, to accomplish an adjustment; communication to accomplish an adjustment is also indicated in FIG. 20 at blocks 730, 740).

A ninth illustrative non-limiting embodiment takes the form of an IMD as in the eighth illustrative non-limiting embodiment, further comprising a mechanical sensor for sensing a patient's posture or activity level, wherein the adjustment means is configured to use an output of the mechanical sensor in addition to the Q-wave to LV R-wave peak timing when determining that the LCP should adjust a therapy regimen. (inclusion of such a sensing circuit is indicated at block 726 of FIG. 20 and may take the various forms noted in association with block 726).

A tenth illustrative non-limiting embodiment takes the form of an IMD as in either of the eighth or ninth illustrative non-limiting embodiments, wherein the adjustment means is configured to include a plurality of modes for determining that an adjustment to the LCP therapy regimen is needed including: a first mode for use with an LCP implanted in or in a tributary to the coronary sinus; and a second mode for use with an LCP implanted in the LV (such a multi-mode solution is indicated in FIG. 20, at block 706).

An eleventh illustrative, non-limiting embodiment takes the form of an IMD as in any of the eighth to tenth illustrative non-limiting embodiments, further comprising composite cycle means configured to calculate a composite cardiac cycle signal using at least two detected cardiac cycles (such composite means may take the form of a dedicated circuitry or stored instruction set for execution by a processor or controller to perform as noted at block 722 of FIG. 20, for example), and the AV interval means is configured to calculate the measure of Q-wave to LV R-wave peak timing using Q-wave information from the composite cycle means.

A twelfth illustrative, non-limiting embodiment takes the form of an IMD as in any of the eighth to eleventh illustrative non-limiting embodiments, wherein the AV interval means is configured to identify a Q-wave using the sensed cardiac signal, and to obtain timing information from the LCP regarding an LV R-wave occurring in the same cardiac cycle as the identified Q-wave by use of the IMD communication means communicating with the LCP, and thereby calculate the Q-wave to LV R-wave peak timing (a cooperative mode is indicated at FIG. 20, block 724, and is also illustrated in FIG. 19).

A thirteenth illustrative, non-limiting embodiment takes the form of an implantable medical device system comprising: a leadless cardiac pacemaker (FIG. 16, at 450) comprising electrodes (FIG. 16, at 464, 466, 468) for therapy output and/or cardiac signal reception, LCP communication means for communicating with at least the IMD (FIG. 16, block 452), pulse generator means for generating pacing output signals (FIG. 16, block 454), the pulse generator means operatively coupled to the electrodes for delivery of pacing therapy; and an IMD as in any of the eighth to twelfth illustrative, non-limiting embodiments; wherein the LCP further comprises a processing module (FIG. 16, block 460) for processing communications from the IMD and effecting changes to therapy provided by the pulse generator means in response to communications from the IMD.

A fourteenth illustrative, non-limiting embodiment takes the form of a system as in the thirteenth illustrative, non-limiting embodiment, wherein the LCP pulse generator module is adapted to deliver a plurality of pacing therapies and then to pause for at least one cardiac cycle to allow the IMD to analyze the intrinsic Q-wave to LV R-wave peak timing (use of such a pause is discussed above and is also illustrated in FIG. 20 at 716).

A fifteenth illustrative, non-limiting embodiment takes the form of a system as in the fourteenth illustrative, non-limiting embodiment, wherein the LCP comprises R-wave detection means for sensing an intrinsic ventricular activation during the pause, and the LCP communications means is adapted to communicate timing of the sensed intrinsic ventricular activation to the IMD for use by the AV interval means of the IMD (such a configuration may include dedicated circuitry, a dedicated state of a state machine, or operational instructions stored in a memory for execution by a controller or processor to perform as illustrated in the block diagram of FIG. 19, and or in a cooperative manner as indicated at 724 of FIG. 20).

Each of these non-limiting embodiments can stand on its own, or can be combined in various permutations or combinations with one or more of the other embodiments.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution at or other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable medical device (IMD) configured for use with a leadless cardiac pacemaker (LCP) implanted in the left ventricle or coronary sinus of a patient, the IMD adapted to communicate with the LCP while implanted using wireless or conducted communication, the IMD comprising:
   a plurality of electrodes for sensing cardiac electrical activity;
   operational circuitry for analyzing the sensed cardiac electrical activity by:
   identifying one or more cardiac cycles;
   calculating a measure of Q-wave to R-wave timing for one or more cardiac cycles; and
   communicating to the LCP to cause the LCP to adjust a therapy regimen using at least the measure of Q-wave to R-wave timing.

2. The IMD as in claim 1 further comprising a posture sensor for sensing a patient's posture, wherein the operational circuitry is configured to calculate an adjustment to the LCP therapy regimen by determining an optimal Q-wave to LV pace timing using the measured Q-wave to R-wave timing and the patient posture.

3. The IMD as in claim 1 wherein the operational circuitry is configured to identify a plurality of at least 2 cardiac cycles and calculate a composite cardiac cycle signal, and to calculate the measure of Q-wave to R-wave timing using the composite cardiac cycle signal.

4. The IMD as in claim 1 wherein the operational circuitry is configured to include a plurality of modes for calculating an adjustment to the LCP therapy including:
   a first mode for use with an LCP implanted in or in a tributary to the coronary sinus; and
   a second mode for use with an LCP implanted in the LV.

5. The IMD as in claim 1 wherein the operational circuitry is configured such that calculating a measure of Q-wave to R-wave timing for one or more cardiac cycles includes calculating a measure of Q-wave to LV R-wave peak timing, which is performed by identifying the Q-wave in the cardiac signal sensed by the IMD, and obtaining timing information from the LCP regarding an LV R-wave occurring in the same cardiac cycle as the identified Q-wave.

6. The IMD as in claim 1 wherein the operational circuitry is configured such that calculating a measure of Q-wave to R-wave timing is performed by:
   identifying a plurality of cardiac cycles,
   calculating a composite cardiac cycle signal for the plurality of cardiac cycles;
   identifying a Q-wave in the composite cardiac cycle signal; and
   using the identified Q-wave to calculate the Q-wave to R-wave timing.

7. The IMD of claim 1 wherein the operational circuitry is configured for calculating a measure of Q-wave to R-wave timing for one or more cardiac cycles during a pause in therapy delivery by the LCP.

8. An implantable medical device system comprising:
   a leadless cardiac pacemaker (LCP) configured for implantation in the left ventricle or coronary sinus of a patient, the LCP comprising LCP electrodes for therapy output and/or cardiac signal reception, an LCP communication module for communicating with at least the IMD, an LCP pulse generator module for generating pacing output signals, and an LCP processing module for managing a therapy regimen provided via the LCP pulse generator module, the LCP processing module responsive to commands received by the LCP communication circuit;

an implantable medical device (IMD) adapted for placement in or on a patient, comprising IMD electrodes for sensing cardiac electrical activity, an IMD communication circuit for communicating at least with the LCP communication circuit, and IMD operational circuitry for analyzing the sensed cardiac electrical activity by:
identifying one or more cardiac cycles;
calculating a measure of Q-wave to R-wave timing for one or more cardiac cycles; and
using the IMD communication circuitry to communicate to the LCP to cause the LCP to adjust a therapy regimen using at least the measure of Q-wave to R-wave timing.

9. The system of claim 8 wherein the IMD further comprises a posture sensor for sensing a patient's posture, wherein the IMD operational circuitry is configured to calculate an adjustment to the LCP therapy regimen by determining an optimal Q-wave to LV pace timing using the measured Q-wave to R-wave timing and the patient posture.

10. The system of claim 8 wherein the IMD operational circuitry is configured to identify a plurality of at least 2 cardiac cycles and calculate a composite cardiac cycle signal, and to calculate the measure of Q-wave to R-wave timing using the composite cardiac cycle signal.

11. The system of claim 8 wherein the IMD operational circuitry is configured to include a plurality of modes for calculating an adjustment to the LCP therapy including:
a first mode for use with an LCP implanted in or in a tributary to the coronary sinus; and
a second mode for use with an LCP implanted in the LV.

12. The system of claim 8 wherein the IMD operational circuitry is configured such that calculating a measure of Q-wave to R-wave timing for one or more cardiac cycles includes calculating a measure of Q-wave to LV R-wave peak timing, which is performed by identifying the Q-wave in the cardiac signal sensed by the IMD, and using the IMD communication circuit to obtain timing information from the LCP regarding an LV R-wave occurring in the same cardiac cycle as the identified Q-wave.

13. The system of claim 8 wherein the IMD operational circuitry is configured such that calculating a measure of Q-wave to R-wave timing is performed by:
identifying a plurality of cardiac cycles,
calculating a composite cardiac cycle signal for the plurality of cardiac cycles;
identifying a Q-wave in the composite cardiac cycle signal; and
using the identified Q-wave to calculate the Q-wave to R-wave timing.

14. The system of claim 8 wherein the IMD and the LCP are configured to operate cooperatively such that the IMD can calculate the measure of Q-wave to R-wave timing for one or more cardiac cycles during a pause in therapy delivery by the LCP.

15. The system of claim 8 wherein the LCP processing module is adapted to interrupt the therapy output of the LCP pulse generator to pause for at least one intrinsic cardiac cycle to allow the IMD to analyze the intrinsic Q-wave to LV R-wave peak timing.

16. The system of claim 8 wherein the LCP comprises an LCP sensing module adapted to sense an intrinsic R-wave during the pause, and the LCP processing module is adapted to cause the LCP communication module to communicate timing of the sensed intrinsic R-wave to the IMD for use in calculating the Q-wave to R-wave timing.

17. A method of operation in an implantable system, the system including:
a leadless cardiac pacemaker (LCP) configured for implantation in the left ventricle or coronary sinus of a patient, the LCP comprising LCP electrodes for therapy output and/or cardiac signal reception, an LCP communication module for communicating with at least the IMD, an LCP pulse generator module for generating pacing output signals, and an LCP processing module for managing a therapy regimen provided via the LCP pulse generator module, the LCP processing module responsive to commands received by the LCP communication circuit;
an implantable medical device (IMD) adapted for placement in or on a patient, comprising IMD electrodes for sensing cardiac electrical activity, an IMD communication circuit for communicating at least with the LCP communication circuit;
the method comprising:
identifying one or more cardiac cycles in each of the IMD and the LCP;
calculating a measure of Q-wave to R-wave timing for one or more cardiac cycles using data captured by each of the IMD and the LCP; and
the LCP adjusting a pacing therapy regimen using at least the measure of Q-wave to R-wave timing.

18. The method of claim 17 wherein the IMD further comprises a posture sensor for sensing a patient's posture, wherein the method further includes:
the IMD operational circuitry determining a patient posture using an output from the posture sensor;
the IMD calculating and communicating an adjustment to the LCP therapy regimen by determining an optimal Q-wave to LV pace timing using the measured Q-wave to R-wave timing and the patient posture.

19. The method of claim 17 wherein the step of calculating a measure of Q-wave to R-wave timing for one or more cardiac cycles includes the IMD calculating a measure of Q-wave to LV R-wave peak timing, and is performed by:
the IMD operational circuitry identifying the Q-wave in the cardiac signal sensed by the IMD;
the LCP processing module identifying an LV R-wave occurring in the same cardiac cycle as the identified Q-wave;
the LCP communicating timing of the identified LV R-wave to the IMD; and
the IMD operational circuitry determining the Q-wave to LV R-wave peak timing.

20. The method of claim 17 wherein the step of calculating a measure of Q-wave to R-wave timing for one or more cardiac cycles includes the LCP calculating a measure of Q-wave to LV R-wave peak timing, and is performed by:
the IMD operational circuitry identifying the Q-wave in the cardiac signal sensed by the IMD;
the LCP processing module identifying an LV R-wave occurring in the same cardiac cycle as the identified Q-wave;
the IMD communicating timing of the Q-wave to the LCP; and the LCP processing module determining the Q-wave to LV R-wave peak timing.

* * * * *